US011918427B2

(12) United States Patent
Leeson et al.

(10) Patent No.: US 11,918,427 B2
(45) Date of Patent: *Mar. 5, 2024

(54) REDUCTION OR GUIDANCE COPING

(71) Applicant: James R. Glidewell Dental Ceramics, Inc., Newport Beach, CA (US)

(72) Inventors: David Leeson, North Tustin, CA (US); Terry Reed, Midway City, CA (US); Summer Ree Takenaka, Fullerton, CA (US); Babak Manafighazani, Rancho Santa Margarita, CA (US); Andrey Lebedev, Moscow (RU)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/830,755

(22) Filed: Jun. 2, 2022

(65) Prior Publication Data
US 2022/0287807 A1 Sep. 15, 2022

Related U.S. Application Data

(63) Continuation of application No. 16/918,586, filed on Jul. 1, 2020, now Pat. No. 11,351,015.

(60) Provisional application No. 62/869,331, filed on Jul. 1, 2019.

(51) Int. Cl.
*A61C 13/00* (2006.01)
*A61C 5/77* (2017.01)
*G16H 50/50* (2018.01)

(52) U.S. Cl.
CPC ........... *A61C 13/0004* (2013.01); *A61C 5/77* (2017.02); *G16H 50/50* (2018.01)

(58) Field of Classification Search
CPC ........... A61C 13/0004; A61C 13/0019; A61C 8/0001
See application file for complete search history.

(56) References Cited

U.S. PATENT DOCUMENTS

| 5,683,243 A | 11/1997 | Andreiko et al. |
| 6,244,861 B1 | 6/2001 | Andreiko et al. |
| 6,398,548 B1 | 6/2002 | Muhammad et al. |

(Continued)

FOREIGN PATENT DOCUMENTS

| JP | 2007521068 A | 8/2007 |
| WO | 2005004743 A2 | 1/2005 |
| WO | 2010068676 A2 | 6/2010 |

OTHER PUBLICATIONS

Hong-Tzong Yau, Computer-aided Framework Design for Digital Dentistry, Computer-Aided Design and Applications, 2008 CAD Solutions, LLC., in 10 pages.

*Primary Examiner* — Jason L Vaughan
(74) *Attorney, Agent, or Firm* — Charles Fowler

(57) ABSTRACT

A computer-implemented method of generating a reduction coping includes receiving a digital model comprising a virtual preparation tooth, determining one or more virtual reduction regions on the virtual preparation tooth, and generating a virtual reduction coping comprising one or more exposed regions corresponding to the one or more virtual reduction regions. A method of generating a physical reduction coping includes receiving a 3D digital model of a virtual reduction coping and performing additive manufacturing to generate a physical reduction coping from the virtual reduction coping.

16 Claims, 18 Drawing Sheets

(56) References Cited

U.S. PATENT DOCUMENTS

| | | | |
|---|---|---|---|
| 6,554,611 B2 | 4/2003 | Chishti et al. | |
| 6,616,444 B2 | 9/2003 | Andreiko et al. | |
| 7,228,191 B2* | 6/2007 | Hofmeister | B33Y 80/00 700/98 |
| 7,555,403 B2* | 6/2009 | Kopelman | A61C 9/004 433/213 |
| 8,033,828 B2* | 10/2011 | Coopersmith | A61C 8/0001 433/136 |
| 8,047,847 B2 | 11/2011 | Kaufmann et al. | |
| 8,200,462 B2* | 6/2012 | Marshall | A61C 13/0004 703/11 |
| 8,386,062 B2* | 2/2013 | Yau | A61C 8/0001 700/98 |
| 8,628,327 B1* | 1/2014 | Blaisdell | A61C 8/0001 433/213 |
| 9,895,209 B2* | 2/2018 | Blaisdell | A61C 13/0001 |
| 10,016,260 B2* | 7/2018 | Blaisdell | A61C 8/0001 |
| 10,406,753 B2 | 9/2019 | Kopelman et al. | |
| 10,568,720 B2* | 2/2020 | Liston | A61C 8/008 |
| 11,185,394 B2* | 11/2021 | Nikolskiy | A61C 13/0004 |
| 11,351,015 B2* | 6/2022 | Leeson | A61C 5/77 |
| 2003/0235803 A1 | 12/2003 | Nikolskiy et al. | |
| 2004/0197728 A1 | 10/2004 | Abolfathi et al. | |
| 2006/0115793 A1 | 6/2006 | Kopelman et al. | |
| 2007/0141536 A1* | 6/2007 | Provost | A61C 13/0004 433/223 |
| 2007/0172787 A1* | 7/2007 | Fornoff | A61C 13/0004 433/3 |
| 2007/0211081 A1 | 9/2007 | Quadling et al. | |
| 2009/0162813 A1 | 6/2009 | Glor et al. | |
| 2009/0325125 A1 | 12/2009 | DiAngelo et al. | |
| 2010/0151417 A1 | 6/2010 | Nilsson et al. | |
| 2010/0191510 A1 | 7/2010 | Kopleman | |
| 2011/0038514 A1 | 2/2011 | Weigl | |
| 2011/0196654 A1 | 8/2011 | Genest et al. | |
| 2012/0139142 A1 | 6/2012 | Van Der Zel | |
| 2015/0056576 A1 | 2/2015 | Nikolskiy et al. | |
| 2015/0272704 A1* | 10/2015 | Watson | A61C 9/0046 433/76 |
| 2018/0132982 A1 | 5/2018 | Nikolskiy et al. | |
| 2018/0368956 A1* | 12/2018 | Fisker | G06F 30/00 |
| 2019/0083208 A1* | 3/2019 | Hansen | A61C 13/0004 |
| 2021/0038350 A1* | 2/2021 | Otawa | A61C 13/0004 |
| 2023/0075448 A1 | 3/2023 | Kopelman et al. | |

* cited by examiner

REDUCTION OR GUIDANCE COPING

CROSS-REFERENCE TO RELATED APPLICATIONS

This application is a continuation of U.S. patent application Ser. No. 16/918,586, filed Jul. 1, 2020, which claims priority to and the benefit of U.S. Provisional Patent Application No. 62/869,331, filed Jul. 1, 2019, each of which is hereby incorporated by reference in its entirety.

BACKGROUND

Conventional techniques for fitting a patient with a restoration typically involve a dentist first assessing a patient's dentition and determining a preparation tooth on which the restoration will be positioned. The dentist then prepares the preparation tooth by reducing its size to make space for the restoration. The dentist then takes an impression of the teeth with the preparation tooth. The impression can be made by using an impression mold or intraoral scanning, for example. The dentist then sends the impression to a dental laboratory, which creates a stone model of the patient's dentition to use in designing the crown. In many cases, the dental laboratory uses a guide to determine there is insufficient occlusal clearance because the dentist has not removed enough of the preparation tooth to provide enough space between the affixed crown and the surrounding teeth, such as the opposing tooth. In such cases, the dental technician creates a reduction coping.

A reduction coping is a tool created by a dental laboratory to remove additional material from a prepared tooth when the initial preparation did not allow enough occlusal space. Conventionally, these are produced by the technician who makes a coping over the preparation tooth of the stone model and then grinds away the stone model material to provide sufficient occlusal space so that the dental laboratory can manufacture the crown to fall within required minimum thickness guidelines. The coping then has a hole that shows the doctor where material should be removed from the prep. The coping itself is conventionally thermoformed or hand waxed. The reduction coping allows the dentist to adjust the prep and deliver the crown without sending another impression back to the lab. A guidance coping performs a similar function and is made in the same way but is to correct draw or path of insertion problems with a preparation instead of insufficient occlusal space.

If the lab receives an intraoral scan or scans the impression instead of making a stone model, there is no way of reducing the preparation and no physical model to thermoform or wax the coping. The only option would be to print a physical model from the scan and then modify it by hand before scanning it again. This can be inefficient and can introduce dimensional errors.

When producing a coping in a high volume production environment where several different patients copings can be produced together, it can be challenging and error prone to identify each one.

Another problem with reduction copings can be that they are very small and difficult to handle and often need to be taken in and out of the patients mouth many times during the reduction process.

SUMMARY

Disclosed is a computer-implemented method of generating a reduction coping. The method can include receiving a digital model comprising a virtual preparation tooth, determining one or more virtual reduction regions on the virtual preparation tooth, and generating a virtual reduction coping comprising one or more exposed regions corresponding to the one or more virtual reduction regions.

Also disclosed is a method of generating a physical reduction coping. The method can include receiving a 3D digital model of a virtual reduction coping and performing additive manufacturing to generate a physical reduction coping from the virtual reduction coping.

DETAILED DESCRIPTION

Figure 1:
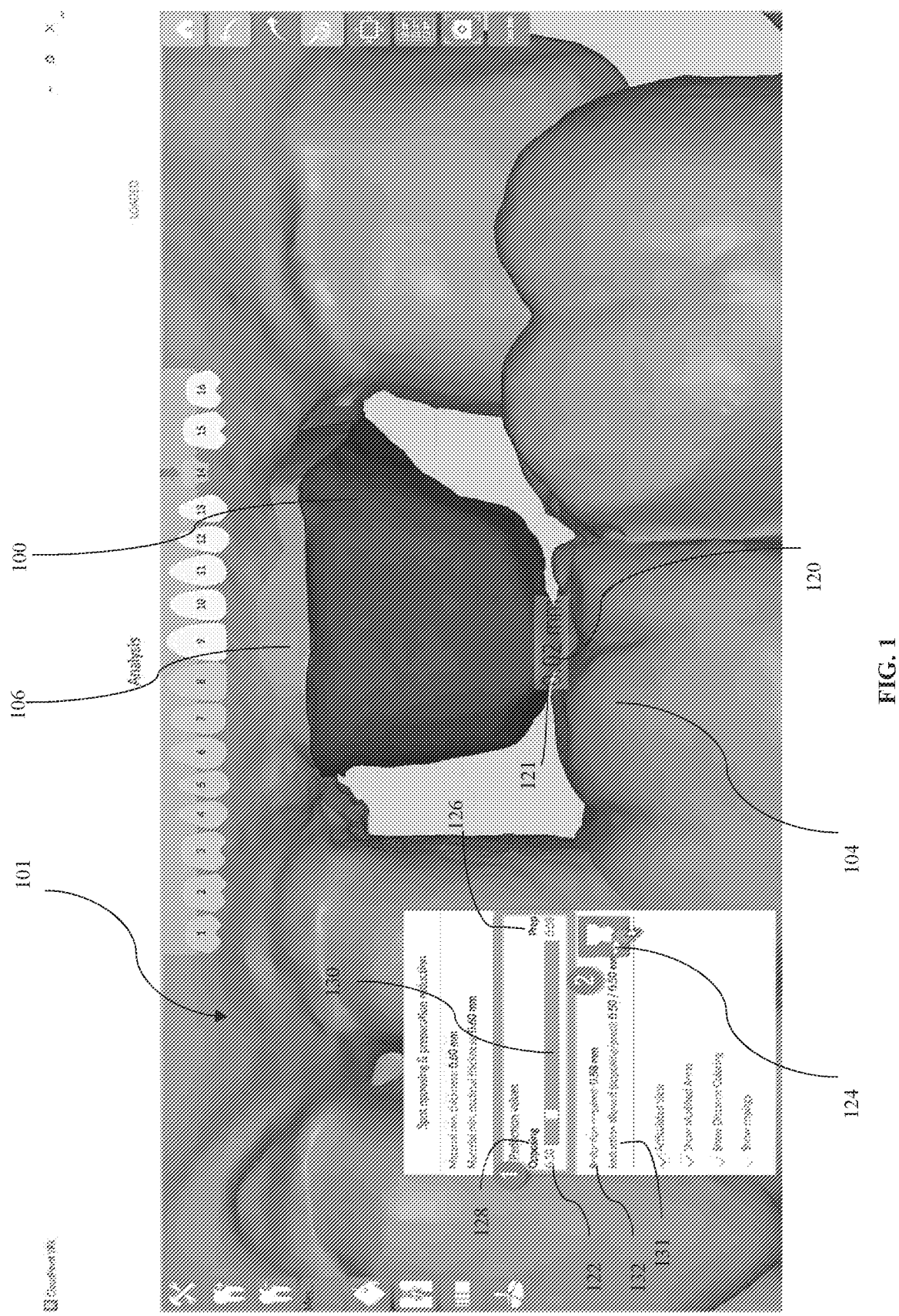
FIG. 1 illustrates a graphic representation of a digital model with a virtual preparation tooth, a virtual opposing tooth, and surrounding dentition provided by a dental design program according to some embodiments.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. The Figures (FIGS.) and the following description describe certain embodiments by way of illustration only. One skilled in the art will readily recognize from the following description that alternative embodiments of the structures and methods illustrated herein may be employed without departing from the principles described herein.

Some embodiments include a computer-implemented method of generating a reduction coping. The computer-implemented method can include, for example, receiving a 3D digital model with a virtual preparation tooth, determining one or more virtual reduction regions on the virtual preparation tooth, and generating a virtual reduction coping with one or more exposed regions corresponding to the one or more virtual reduction regions. In some embodiments, the computer-implemented method receives a digital model of a dental impression. The digital dental impression can be from an intraoral scan of a patient's dentition or from a CT scan of a physical dental impression.

Exemplary embodiments of methods and systems for generating a virtual and/or physical guidance/reduction coping are described herein. The computer-implemented methods of generating a virtual and/or physical guidance/reduction coping described herein can use a digital model of at least a portion of a patient's oral situation as a starting point for the process. FIG. 1 illustrates one example of a digital model 101 that can be used. The digital model 101 can be generated by scanning a physical impression using any scanning technique known in the art including, but not limited to, for example, optical scanning, CT scanning, etc. or by intraoral scanning of the patient's mouth (dentition). A conventional scanner typically captures the shape of the physical impression/patient's dentition in 3 dimensions during a scan and digitizes the shape into a 3 dimensional digital model. The digital model 101 can include multiple interconnected polygons in a topology that corresponds to the shape of the physical impression/patient's dentition, for example. In some embodiments, the polygons can include two or more digital triangles. In some embodiments, the scanning process can produce STL, PLY, or CTM files, for example that can be suitable for use with a dental design software, such as FastDesign™ dental design software provided by Glidewell Laboratories of Newport Beach, Calif. One example of CT scanning is described in U.S. Patent Application No. US20180132982A1 to Nikolskiy et al., which is hereby incorporated in its entirety by reference.

The digital model 101 can also be generated by intraoral scanning of the patient's dentition, for example. In some embodiments, an electronic image is obtained by a direct intraoral scan of the patient's teeth. This will typically take place, for example, in a dental office or clinic and be performed by a dentist or dental technician. In other embodiments, the electronic image is obtained indirectly by scanning an impression of the patient's teeth, by scanning a physical model of the patient's teeth, or by other methods known to those skilled in the art. This will typically take place, for example, in a dental laboratory and be performed by a laboratory technician. Accordingly, the methods described herein are suitable and applicable for use in chair side, dental laboratory, or other environments.

In one embodiment, a plurality of scans (e.g., 3-5 scans per quadrant) is performed in order to obtain a suitable image of the patient's anatomy. For example, an occlusal, lingual, and buccal scan may be taken of both the preparation and the opposing jaws. Then, a single scan with the jaws in occlusion may be taken from the buccal perspective to establish the proper occlusion relationship between the preparation jaw and the opposing jaw. Additionally, in some embodiments, interproximal scans are added to capture the contact areas of neighboring teeth. Once the scanning process is completed, a scanning system (not shown in FIGS) can assemble the plurality of scans into a digital model (also referred to as a "scanned model" or "scanned dental model" herein) of the preparation tooth and its surrounding and opposing teeth. The scanned model can be used to design and generate a guidance/reduction coping to be used on the preparation tooth. For example, a dental design program may process and display the scanned model in a user interface on a user device. A user (e.g., a design technician)

operating on the user device can view the scanned dental model and generate a guidance/reduction coping based on the scanned model.

The computer-implemented method can receive the digital model 101 having one or more virtual preparation teeth. The virtual preparation teeth can be prepared, for example, by a user such as a dentist or dental technician, for example using dental design software such as FastDesign™ or other design software known in the art in some embodiments. In some embodiments, the computer-implemented method can receive the digital model 101 that can include a first virtual prepared tooth 100 and its corresponding margin line, virtual preparation tooth margin 106, for example. The virtual preparation tooth margin 106 can be determined using any technique known in the art. For example, in some embodiments, a technician (user) can manually mark the margin line using an input device such as a mouse or touch screen while viewing the digital model 101 on a display. Another technique to determine virtual preparation teeth and their corresponding margin line is described in, for example, *Computer-aided Framework Design for Digital Dentistry* by Hong-Tzong Yau, Chien-Yu Hsu, Hui-Lang Peng and Chih-Chuan Pai in Computer-Aided Design & Applications, 5 (5), 2008, 667-675, the entirety of which is hereby incorporated by reference. Other techniques known in the art to specify digital preparation teeth and their corresponding margin line can be used.

More or fewer virtual preparation teeth can be present in the digital model 101 in some embodiments. In some embodiments, at least one virtual tooth can be prepared to receive a dental restoration. In some embodiments, the dental restoration can be a crown, for example or other restoration.

FIG. 1 illustrates a digital model 101 of a dental impression that is displayed to a user through a graphical user interface ("GUI"). The digital model 101 contains at least one virtual preparation tooth 100 and can include surrounding dental features such as additional surrounding virtual teeth, for example. Other dental features can also be present. As shown in FIG. 1, the additional surrounding virtual teeth can include at least one virtual opposing tooth 104 on a virtual opposing jaw.

In some embodiments, the virtual preparation tooth 100 is a digitized version of a physical a tooth that has already been prepared to receive a physical restoration such as a crown, for example, or other restorations. Thus, in some embodiments, the virtual preparation tooth 100 is typically smaller in size and shaped to have a smooth virtual occlusion surface compared to the surrounding virtual teeth.

In some embodiments, the computer-implemented method digitally can reduce the virtual preparation tooth to address clearance issues. In some embodiments, this can help automate processing which is done manually with physical models, for example. For example, in some cases, the virtual preparation tooth can be reduced when the opposing cannot be reduced, the patient does not want the opposing reduced, or the opposing tooth has already been reduced too much and cannot go any further, or for any other situation/reason.

In some embodiments, the computer-implemented method performs a virtual preparation tooth reduction. In some embodiments, this can be similar to spot opposing, but can reduce the die on the virtual preparation tooth, for example. In some embodiments, the computer-implemented method can automatically identify the area where there is not enough clearance, for example. The computer-implemented method can automatically reduce the area on the virtual preparation tooth 100 to resolve the clearance issue. After reduction, the area can be left with a smooth surface. In some embodiments, screenshots can be automatically generated before and after the reduction, for example. The computer-implemented method can be saved and may be used in analysis.

In some embodiments, a design of a guidance/reduction coping generated from dental CAD software with integrated handle and unique identifier that has been optimized for 3d printing is disclosed. In some embodiments, a virtual reduction coping can be designed in CAD after the virtual margin is marked but before the dental restoration itself is designed, for example. These can essentially create a boolean operation to remove this volume from the virtual preparation tooth, for example. In some embodiments, a virtual reduction coping can then be designed as an offset of the original virtual preparation tooth surface that remains. For example, a first offset to create some clearance and then an additional offset that defines the thickness of the coping in the range 0.3 mm-1 mm. In some embodiments, the dental restoration such as a crown for example can be designed and an output file for 3D printing can be generated, for example.

In some embodiments, the computer-implemented method can automatically and virtually determine one or more virtual reduction regions. In some embodiments, the one or more virtual reduction regions can be on the virtual preparation tooth, for example. In some embodiments, the computer-implemented method can determine one or more necessary virtual reduction regions by detecting an insufficient clearance between one or more surfaces of the virtual preparation tooth 100 and one or more other dental features. For example, in some embodiments, the insufficient clearance can be an insufficient occlusal clearance 120 between an occlusal surface of the virtual preparation tooth 100 and an occlusal surface of a virtual opposing tooth 104. In some embodiments, the computer-implemented method can determine one or more necessary virtual reduction regions due to an insufficient path of insertion between one or more side surface regions of the virtual preparation tooth 100 and the virtual preparation tooth margin boundary 106, for example.

In some embodiments, the computer-implemented method determines an insufficient occlusal clearance by determining a minimum required occlusal clearance between the occlusal surface of the virtual preparation tooth 100 and the virtual opposing tooth 104. The computer-implemented method can determine the minimum required occlusal clearance based on several factors. In some embodiments, the minimum required occlusal clearance can be a minimum restoration thickness. In some embodiments, the computer-implemented method determines the minimum restoration thickness based on a restoration type selected. Restorations can be made of different materials. The material used for a particular restoration can influence the minimum restoration thickness. For example, restorations such as crowns can require a minimum thickness. The computer-implemented method can in some embodiments receive the restoration type and determine a required minimum restoration thickness based on the type of restoration. The computer-implemented method can obtain the required minimum restoration thickness automatically or from a user selection of the minimum restoration thickness. In some embodiments, the minimum required occlusal clearance can be based on the minimum restoration thickness and an adhesive thickness. For example, the minimum required occlusal clearance can be the sum of the minimum restoration thickness and the adhesive thickness. The adhesive can be, for example, cement, and can be arranged on the preparation tooth to attach the restoration. In some embodiments, any additional layers of material between the preparation tooth and the restoration can contribute to the minimum required occlusal clearance. For example, additional layer thickness requirements/values can be added to the minimum restoration thickness and the adhesive thickness to determine the minimum required occlusal clearance. In some embodiments, the minimum required occlusal clearance can be determined by parameters of minimum occlusal clearance, cement gap, material thickness and path of insertion to ensure sufficient draft to seat the restoration.

In some embodiments, the computer-implemented method detects an insufficient virtual occlusal clearance 120 by determining a virtual occlusal clearance 121 between one or more virtual preparation tooth occlusal surfaces and one or more virtual opposing tooth occlusal surfaces is less than the minimum required occlusal clearance. In some embodiments, the computer-implemented method determines the virtual occlusal clearance when a virtual jaw is closed or clenched, or when the virtual preparation tooth 100 and virtual opposing tooth 104 are closest to each other. The computer-implemented method in this way can determine that a height of the virtual preparation tooth 100 and a height of the virtual opposing tooth 104 are too large to accommodate the restoration's minimum restoration thickness between them when the jaw is closed or clenched.

Figure 2:
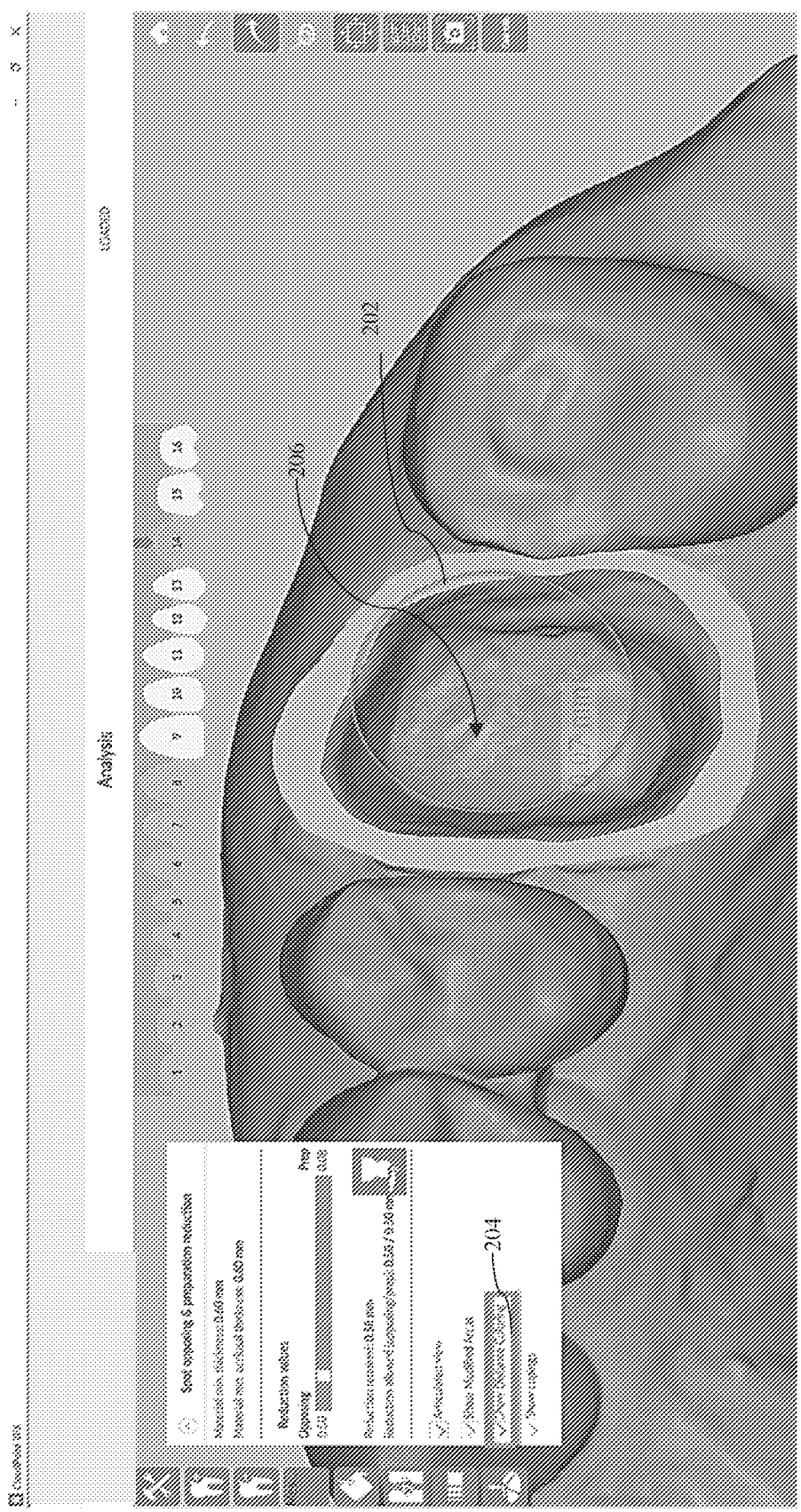
FIG. 2 illustrates a graphic representation of a digital model with a virtual preparation tooth and one or more virtual preparation tooth reduction areas provided by a dental design program according to some embodiments.

To accommodate the restoration between the virtual preparation tooth 100 and the virtual opposing tooth 104, the computer-implemented method can determine a total virtual reduction amount necessary to satisfy the minimum required occlusal clearance. The computer-implemented method can display the total virtual reduction amount on a GUI to illustrate the total reduction necessary. In some embodiments, the total virtual reduction amount is a difference between the virtual occlusal clearance and the minimum required occlusal clearance, for example. In some embodiments, the computer-implemented method can determine a default virtual reduction value. In some embodiments, the computer-implemented method can determine a default distribution 128 of the default virtual reduction amount between the virtual preparation tooth 100 and the virtual opposing tooth 104. For example, in some embodiments, the computer-implemented program can determine a virtual preparation tooth reduction amount 126 and a virtual opposing tooth reduction amount 122, the sum of which is the total virtual reduction amount 132. In some embodiments, the total virtual reduction amount can be adjusted by a user via a graphical user interface element such as the input field. In some embodiments the computer-implemented method can display to the user a graphical user interface element such as slider bar 130 shown in FIG. 1 to adjust the distribution of the total virtual reduction amount 132 between the virtual preparation tooth reduction amount 126 and the virtual opposing tooth reduction amount 122. In some embodiments, the computer-implemented method initially (by default) distributes more or most of the total virtual reduction amount to the virtual opposing tooth reduction amount 122. In some embodiments, if the total virtual reduction amount 132 meets or exceeds a confirmation limit 131, then the case can be flagged for follow up and confirmation with the dentist and the computer-implemented method does not process the case further. The confirmation limit 131 can also be displayed to the user through a GUI element, as can all other values as depicted in the figures. In some embodiments, if the virtual opposing tooth reduction amount 122 meets or exceeds a confirmation limit 131, then the case can be flagged for follow up and confirmation with the dentist and the computer-implemented method does not process the case further. In some embodiments, the confirmation limit can be 0.5 mm, for example. The confirmation limit 131 can be a user configurable value that can be stored in a configuration file which the computer-implemented method can load, for example. Once confirmation is received, a user can release the hold and allow the case to further process. In some embodiments, the computer-implemented method displays information on a GUI as illustrated in FIG. 1 and FIG. 2, thereby allowing a dental technician/user to take a screenshot of the clearance issue with parameters shown by color map and distance number. In some embodiments, this information can be used in a call the doctor if nothing is stated in the prescription, for example. In some embodiments, the screenshot can be shipped with the case back to the doctor, for example. In some embodiments, if a call is needed, the computer-implemented method can designate the case to be on HOLD in a work queue, for example. If a call is not needed, then no HOLD is designated for the case, and work can proceed in some embodiments, for example. In some embodiments, once the lab receives confirmation from the doctor, the computer-implemented method can reopen the case and populate to the queue to perform the reduction, and the technician/user can trigger the reduction in some embodiments, for example.

In some embodiments, the computer-implemented method can determine one or more virtual preparation tooth reduction regions on the virtual preparation tooth. In some embodiments, the computer-implemented method can determine one or more virtual preparation tooth reduction regions as virtual preparation tooth occlusal surface regions where the occlusal clearance is less than the minimum required occlusal clearance. In some embodiments, the computer-implemented method can determine one or more virtual opposing tooth reduction regions as virtual opposing tooth occlusal surface regions where the occlusal clearance is less than the minimum required occlusal clearance. In some embodiments, the total reduction amount can be the difference between the occlusal clearance and the minimum required occlusal clearance. In the example of FIG. 1, the computer-implemented method can analyze the digital dental impression/model and can detect, for example, the occlusal clearance 121. As illustrated in the example in FIG. 1, the occlusal clearance 121 may be very minimal at 0.02 mm. Since the material min. occlusal thickness required is 0.60 mm in the example figure, the computer-implemented method can determine the total virtual reduction requirement 132 to be 0.58 mm, for example. In some embodiments, the user/technician has the option to select the desired amount of reduction to be made to both the virtual opposing tooth and virtual preparation tooth by using slider bar 130, for example. In some embodiments, once the desired amount is selected, the user can press the "Perform Reduction" button, for example.

As shown in the example of FIG. 2, before the user performs the reduction, the computer-implemented method can display a distance coloring map, for example. The distance coloring map can be selected to display by the user using, for example, a distance coloring map check box 204 in some embodiments. The user can utilize this color map to clearly see the affected area. In some embodiments, the computer-implemented method can display the one or more virtual preparation tooth reduction regions on a display. For example, FIG. 2 illustrates a virtual preparation tooth reduction region 206 on the virtual preparation tooth occlusal surface. The computer-implemented method can provide a graphical user interface element to allow a user to adjust the one or more virtual preparation tooth reduction regions 202.

Figure 3:
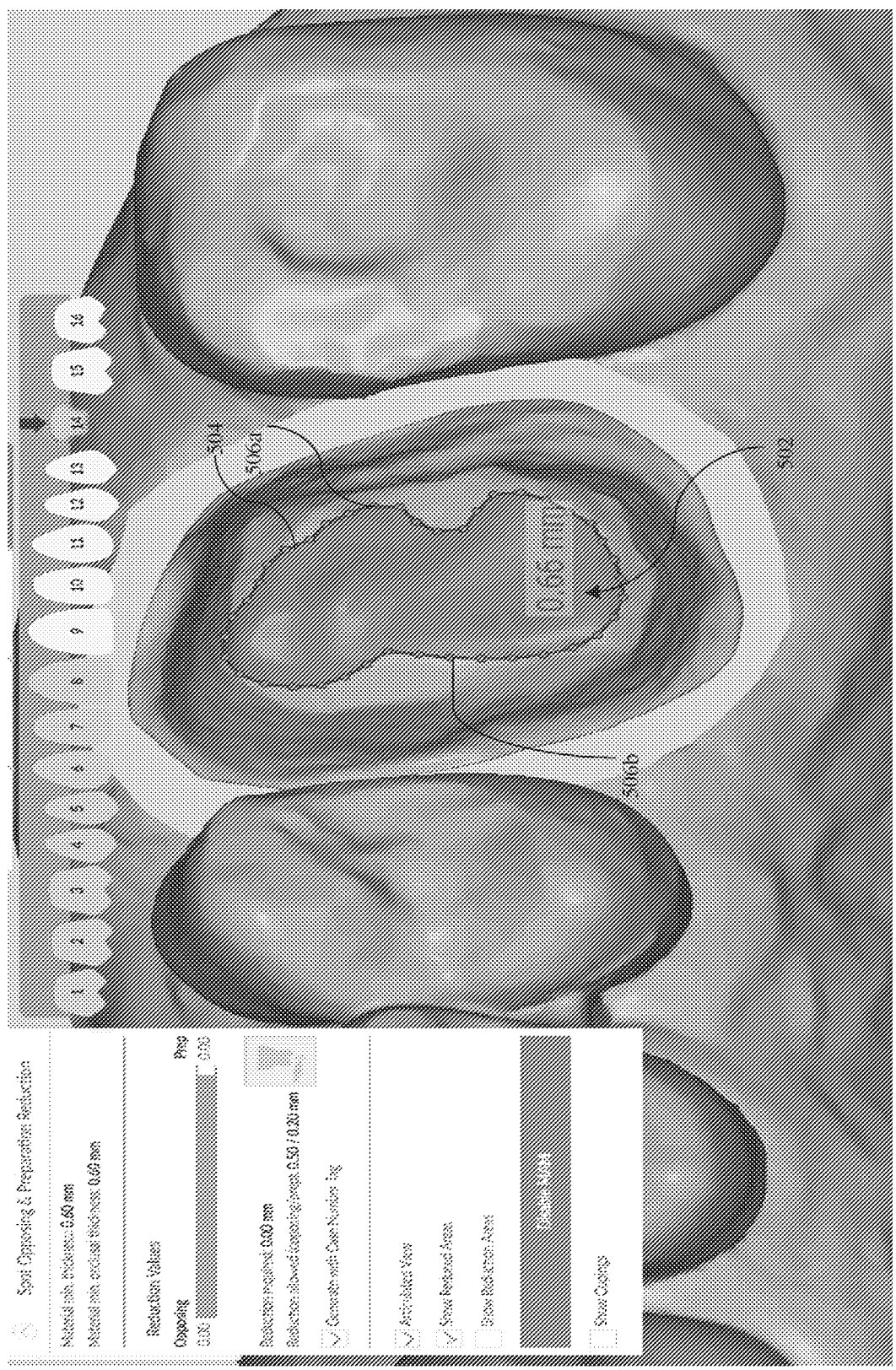
FIG. 3 illustrates a graphic representation of a digital model with a virtual preparation tooth and a reduction region boundary provided by a dental design program according to some embodiments.

As illustrated in example FIG. 3, a reduction region boundary 504 can be altered by a user by accessing handle points 506a and 506b on the reduction region boundary 504 to change the virtual preparation tooth reduction region 502. (Or a virtual opposing tooth reduction region). In some embodiments, the computer-implemented method can also display the one or more virtual opposing tooth reduction regions to the user. In some embodiments, the virtual preparation tooth and opposing tooth reduction regions are displayed in color.

Figure 4:
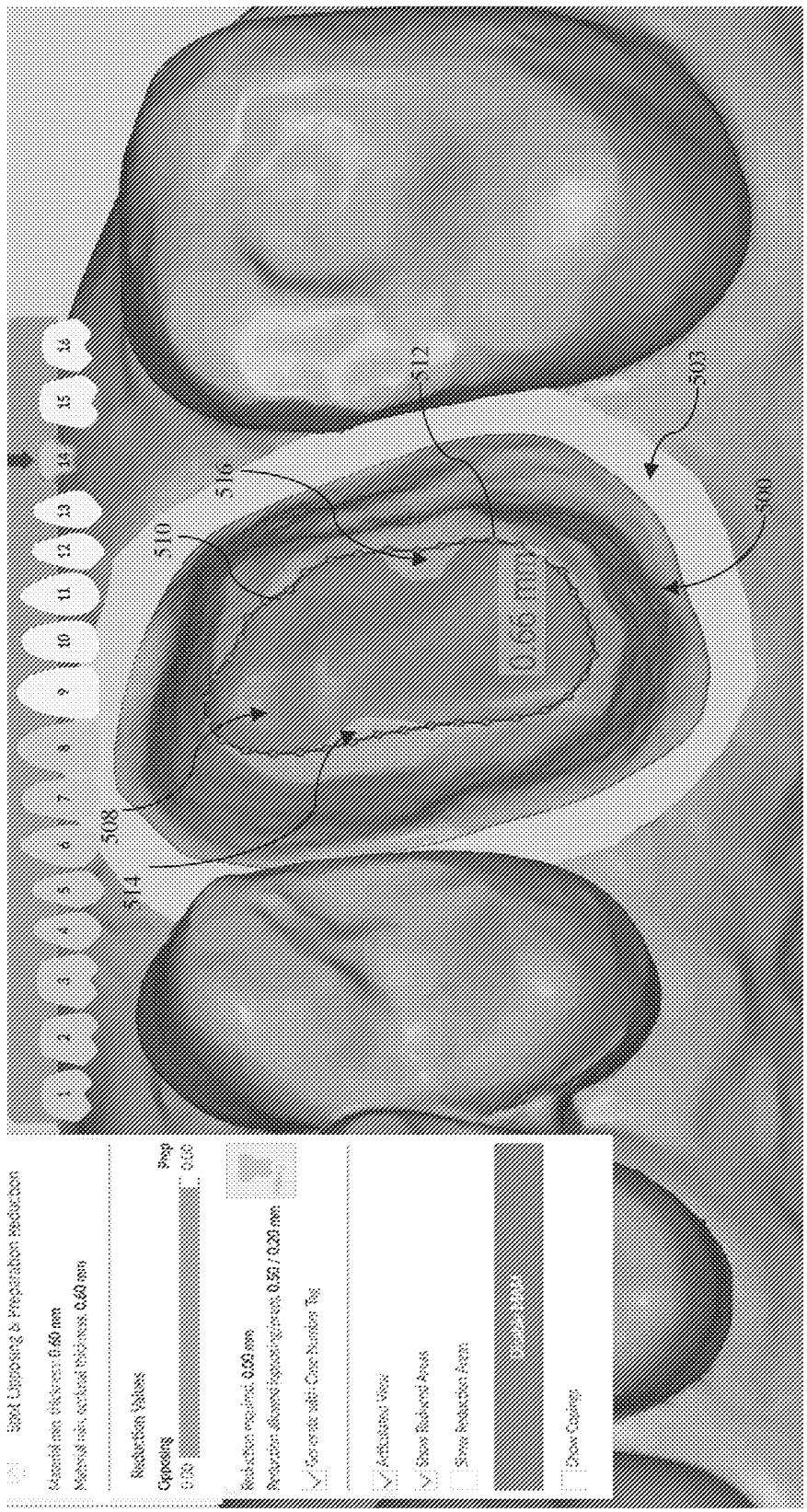
FIG. 4 illustrates a graphic representation of a digital model with a virtual preparation tooth and an adjusted reduction region boundary provided by a dental design program according to some embodiments.

FIG. 4 illustrates an example whereby the user has moved the reduction region boundary 504 from FIG. 3 to a new reduction region boundary 510 with new reduction regions 514 and 516 and new handle points 512, for example. In. this example, the new regions will expand the original reduction region 508.

In some embodiments, the computer-implemented method can perform a virtual reduction of the virtual preparation tooth reduction regions by the virtual preparation tooth reduction amount. In some embodiments, the virtual reduction can be initiated by the user selecting a GUI element such as a perform reduction button 124 as shown in FIG. 1. The computer-implemented method can reduce the virtual preparation tooth reduction regions to produce an even, smooth, and level one or more virtual reduced regions that can blend with surrounding virtual regions. In some embodiments, the computer-implemented method can perform the virtual reduction of the virtual opposing tooth. In some embodiments, the computer-implemented method can perform the virtual reduction in response to a command by the user. In some embodiments, the computer-implemented method performs the virtual reduction by eliminating the virtual reduction regions by the virtual reduction amount. In some embodiments, the computer-implemented method can generate screenshots that can provide information such as color maps illustrating virtual preparation tooth reduction regions and virtual opposing tooth reduction regions, for example. Additional parameters can also be included in the screenshots in some embodiments, for example.

In some embodiments, the computer-implemented method can determine one or more necessary virtual reduction regions due to an insufficient virtual path of insertion. In some embodiments, the virtual preparation tooth 100 can include a preparation tooth virtual margin 503 as shown in FIG. 4. In some embodiments, the computer-implemented method virtually die-trims a virtual margin 503 around the virtual preparation tooth 500. This can include, for example, the computer-implemented method automatically determining a virtual preparation tooth margin 503 around the virtual preparation tooth 500 and/or a user marking the margin manually using an input device as is known in the art. In some embodiments, the virtual preparation tooth margin 503 can be displayed in a graphical user interface to the user as shown in FIG. 4.

Figure 5:
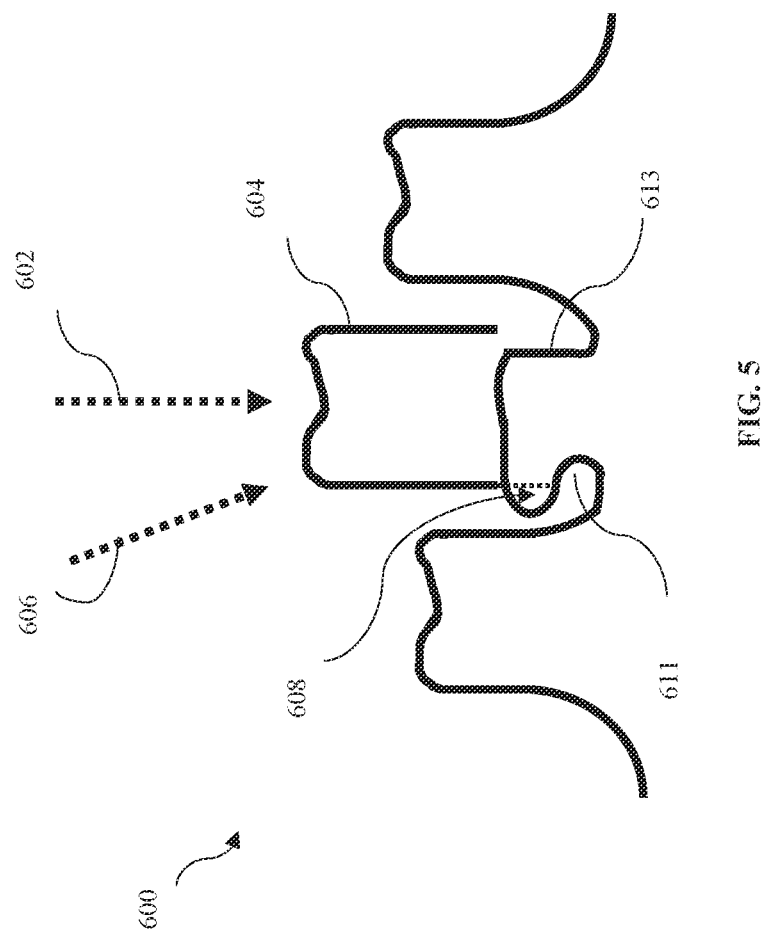
FIG. 5 illustrates a 2D cross section illustration of a portion of a 3D digital model of dentition showing an undercut.

As illustrated in the example 600 of FIG. 5, in some embodiments, the path of insertion is a path the dentist will use to seat a restoration 604 on the margin. FIG. 5 shows a 2D cross-section illustration of a portion of a 3D digital model of a patient's dentition. In some embodiments, an initial or default virtual path of insertion 602 can be along an occlusal direction, for example. However, other virtual paths of insertion 606 are possible. In some embodiments, the computer-implemented method sets a default path of insertion that is an optimal path of insertion to minimize undercuts 611. An undercut 611 can cause one or more virtual preparation tooth side surface regions 608 of the virtual preparation tooth 613 to block the margin when viewed from the path of insertion 602 or 606, for example. This can cause restoration seating issues since the restoration in some embodiments can be arranged to maximally connect to the margin, for example. If any portion of the virtual margin is blocked along the path of insertion by one or more virtual preparation tooth side surface regions, then the computer-implemented method can determine that a virtual open margin exists.

Figure 6:
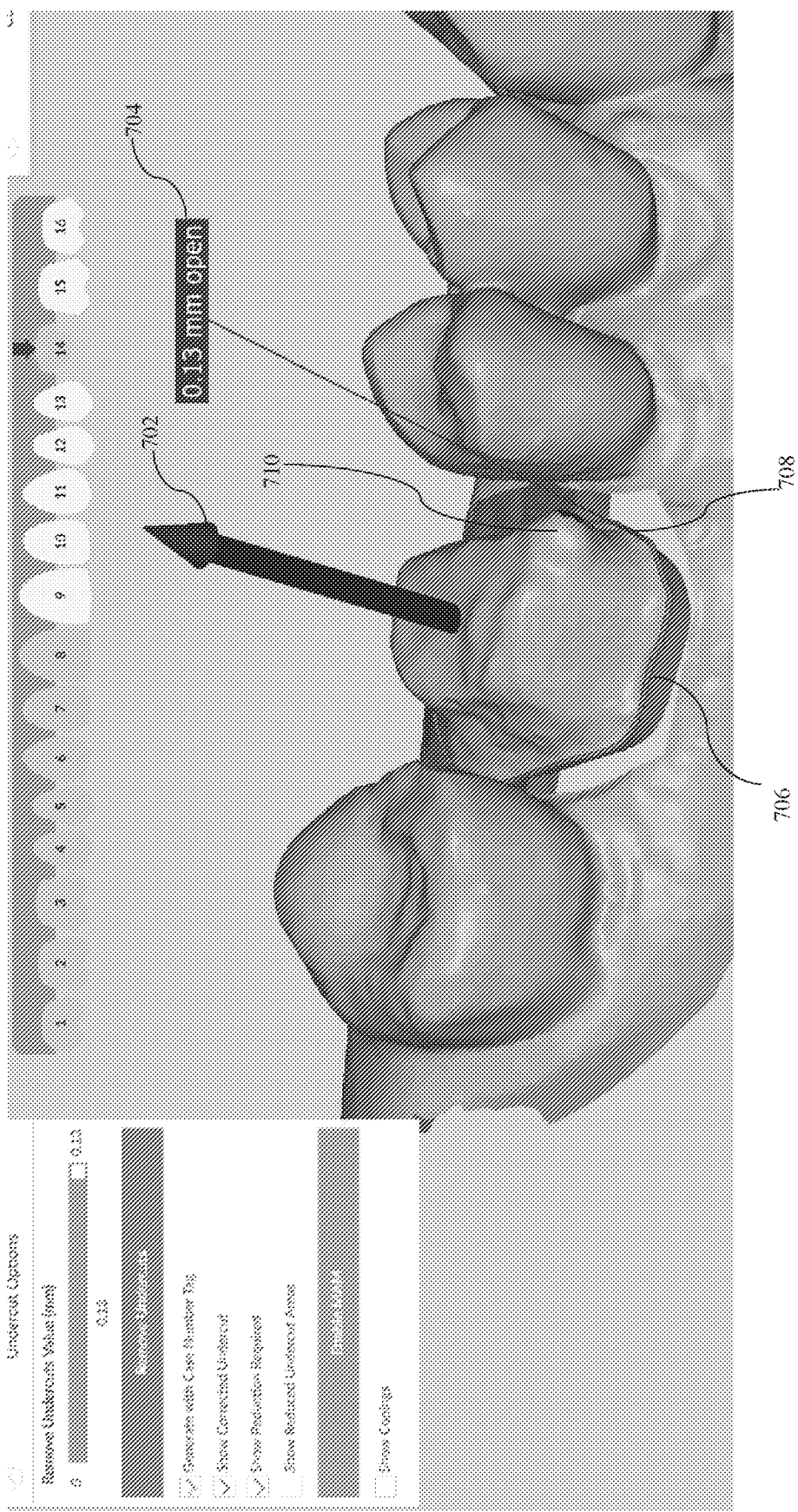
FIG. 6 illustrates a graphic representation of a digital model with a virtual preparation tooth with an open margin provided by a dental design program according to some embodiments.
Figure 7:
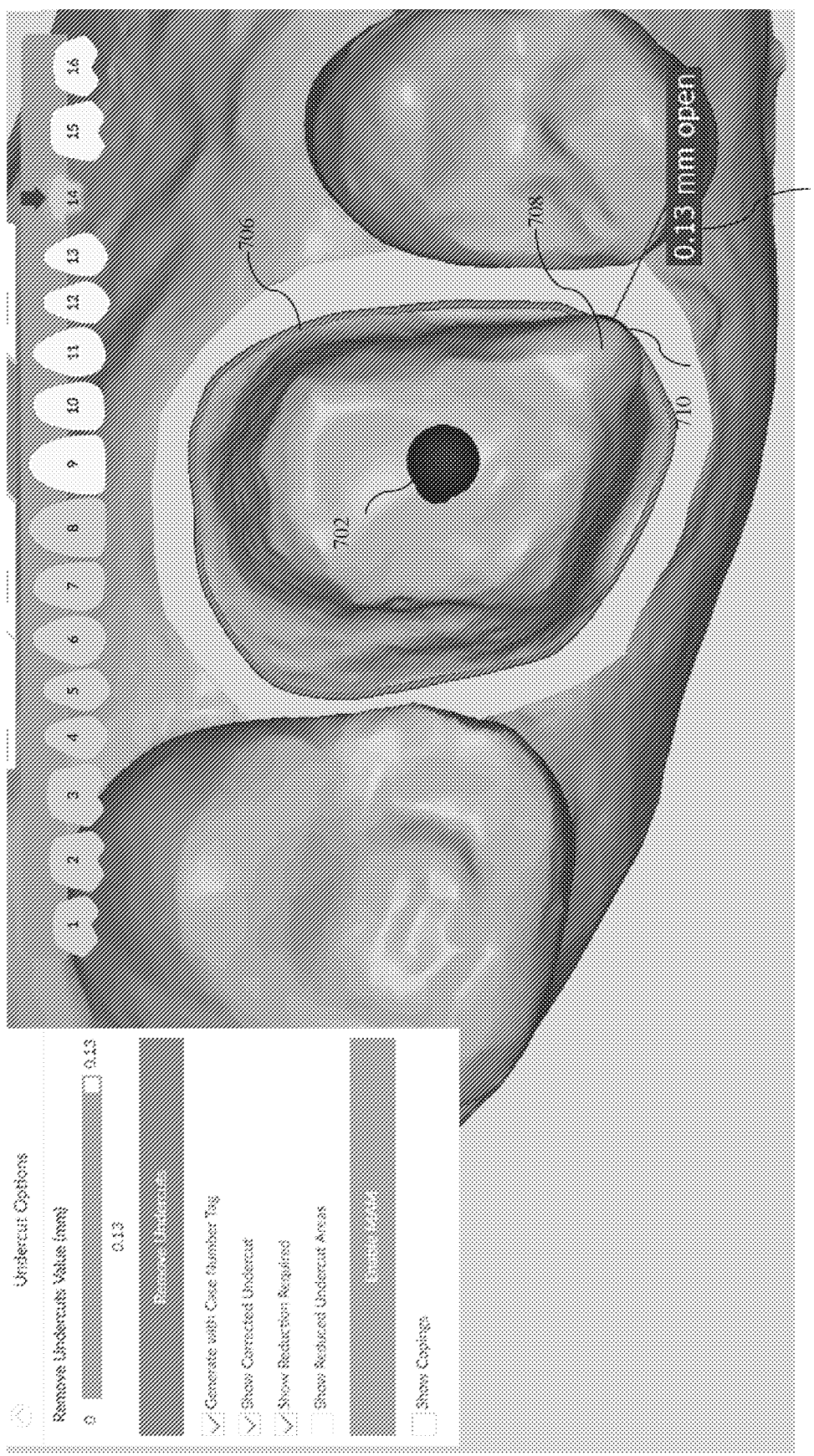
FIG. 7 illustrates a graphic representation of a digital model with a virtual preparation tooth with an open margin as viewed along an occlusion axis.
Figure 8:
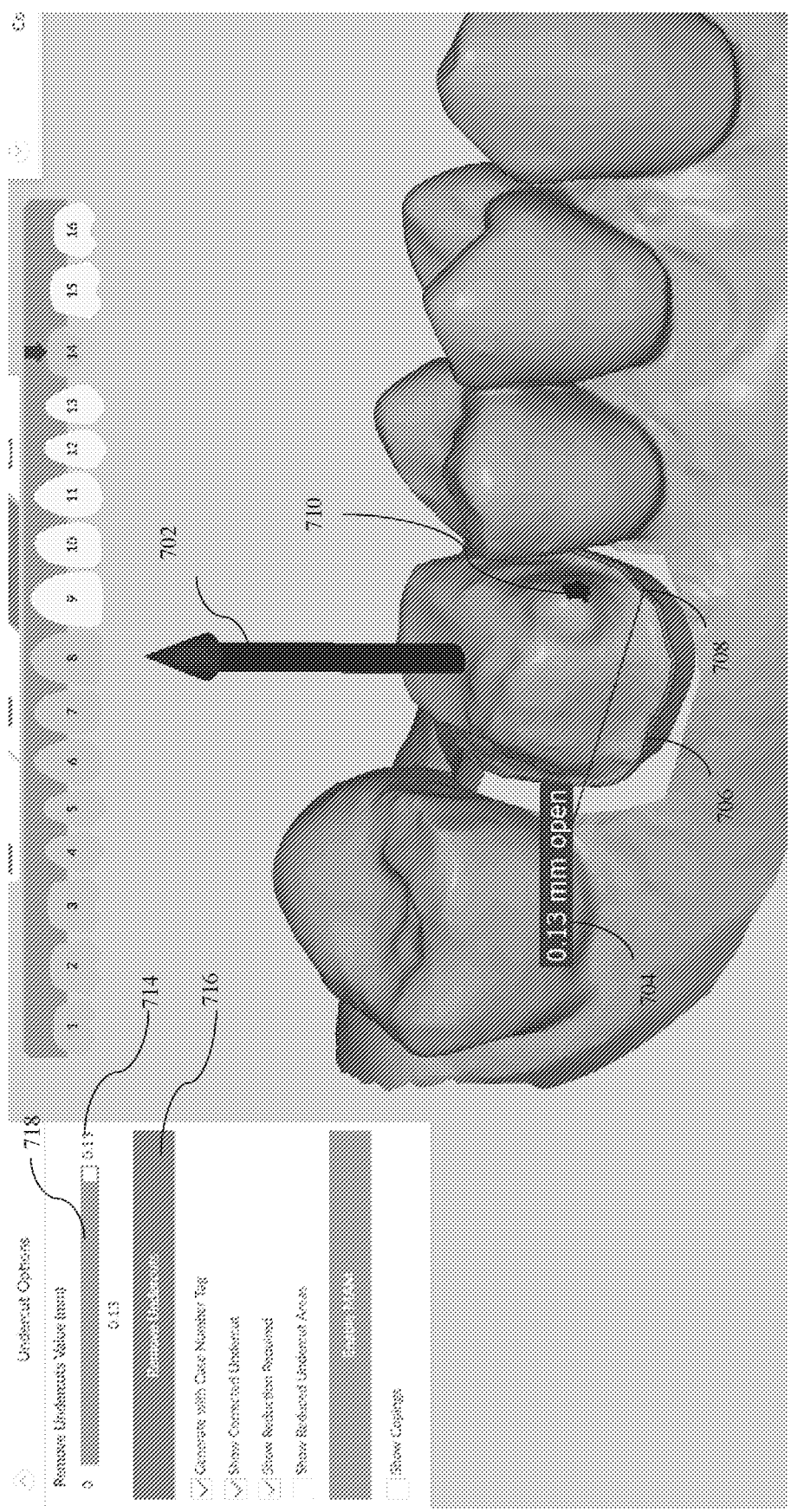
FIG. 8 illustrates a graphic representation of a digital model with a virtual preparation tooth with an open margin provided by a dental design program according to some embodiments.

FIGS. 6-8 illustrate an example of a virtual open margin. FIG. 6 illustrates a path of insertion 702 having a virtual margin 706. Due to the virtual preparation tooth side surface region 710, the virtual preparation tooth has an open virtual margin 708. The computer-implemented method can in some embodiments automatically determine a virtual preparation sidewall reduction value 704 (also called an undercut value). The computer-implemented method can determine this value, for example, by determining how much of the sidewall is causing the open virtual margin 708 when viewed along the path of insertion 702.

FIG. 7 illustrates the same features viewed from the path of insertion 702. As can be seen in the figure, virtual margin 706 is open due to the virtual preparation tooth side surface region 710. As illustrated in FIGS. 7 and 8, in some embodiments, the computer-implemented method determines one or more virtual preparation tooth reduction regions as virtual preparation tooth side surface regions 710 that block the virtual margin 706 when viewed from the point of insertion 702. The computer-implemented method can determine the virtual preparation tooth side surface reduction amount 704 necessary to close the open virtual margin 708 from the point of insertion 702. In some embodiments, the computer-implemented method can determine one or more virtual preparation tooth side surface regions to reduce to close the margin. In some embodiments, the virtual preparation tooth side surface regions to reduce are virtual preparation tooth reduction regions. In some embodiments, the computer-implemented method can perform a virtual undercut reduction to close the virtual margin. This can also be referred to as reducing the virtual preparation tooth side surface regions.

In some embodiments, the computer-implemented method sets a default virtual undercut reduction value and displays a GUI element 718 allowing the user to change the virtual preparation tooth side region reduction amount (virtual undercut reduction value) and showing the open virtual margin amount 714 as illustrated in FIG. 8. In some embodiments, the computer-implemented method provides a GUI element such as virtual button 716 to initiate the virtual reduction of the virtual preparation tooth side surface regions 710. In some embodiments, the computer-implemented method allows the user to change the path of insertion. In some embodiments, the computer-implemented method provides a GUI element such as the arrow showing path of insertion 702 to allow a user to change or adjust the path of insertion.

Figure 9:
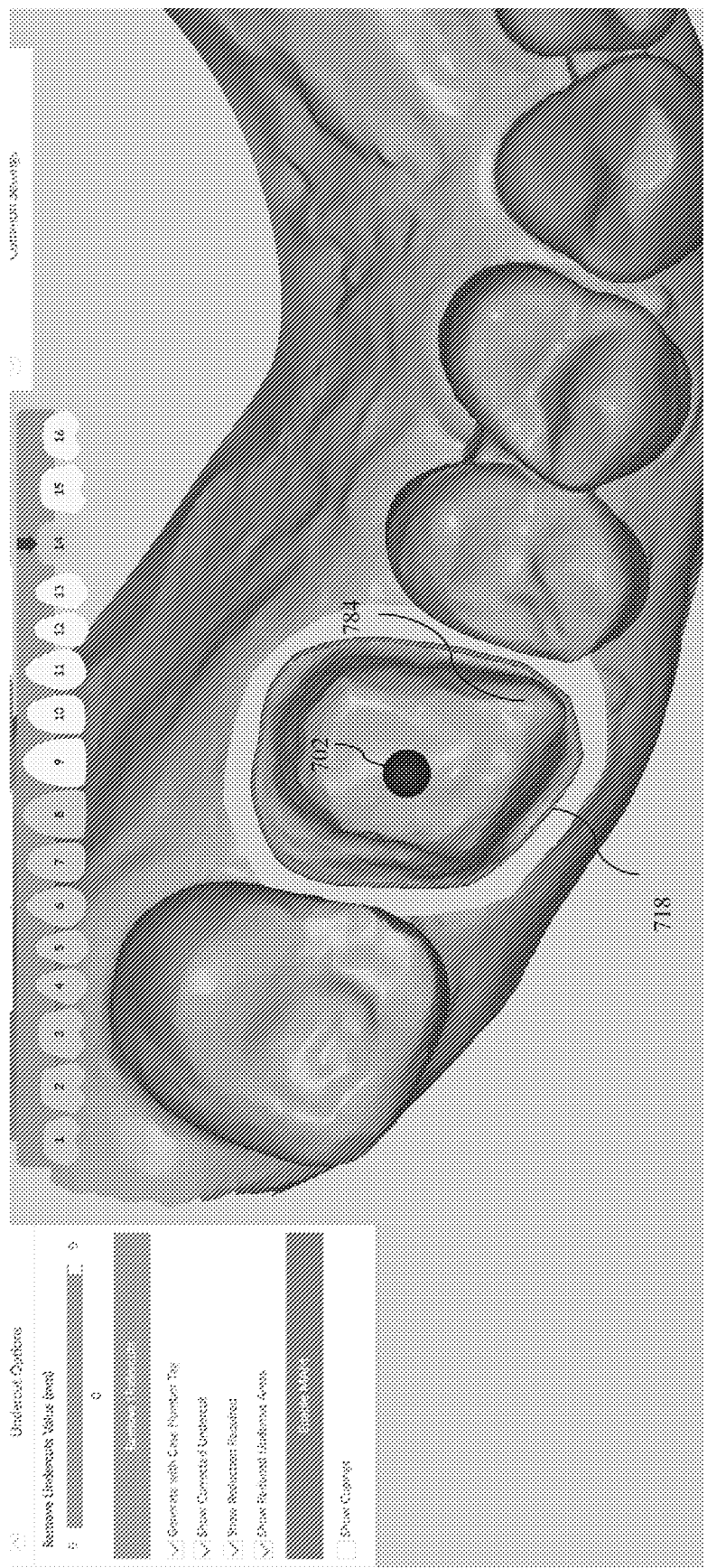
FIG. 9 illustrates a graphic representation of a digital model with a virtual preparation tooth with an open margin that has been closed provided by a dental design program according to some embodiments.

As illustrated in the example of FIG. 9, upon completion of removing the undercut, the virtual margin 718 is closed since the virtual preparation tooth side region no longer blocks the virtual margin 718 from the path of insertion 702. This can provide an exposed undercut removed region 784.

Figure 10:
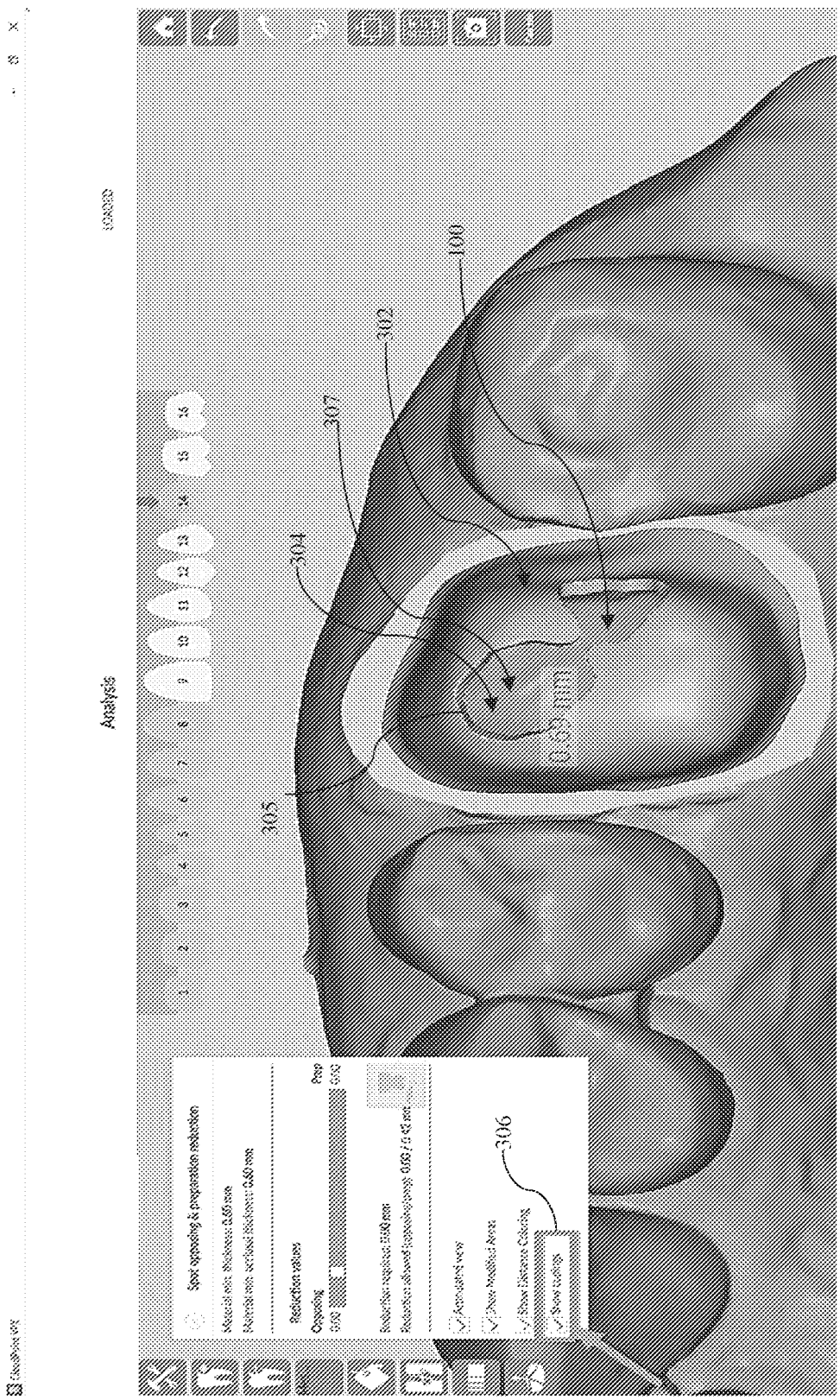
FIG. 10 illustrates a graphic representation of a digital model with a virtual guidance/reduction coping provided by a dental design program according to some embodiments.

As shown in the example of FIG. 10, after the virtual reduction is performed, the computer-implemented method can in some embodiments automatically generate a virtual reduction coping, for example. In some embodiments, the virtual reduction coping can be equipped with holes, or virtual preparation tooth reduction regions, which will help the doctor to reduce the appropriate areas when the patient is chairside. In some embodiments, to enable visibility of the coping, the user selects "Show copings" checkbox 306, for example.

As illustrated in the example FIG. 10, in some embodiments, the computer-implemented method generates a virtual reduction coping 302 dimensioned for optimized fit over the virtual preparation tooth 100 without the adhesive layer. As illustrated in FIG. 10, virtual reduction region 304 has been reduced on the virtual preparation tooth 100. In some embodiments, the virtual reduction coping 302 includes virtual reduction coping material formed around the one or more virtual preparation tooth reduction regions 304 bounded by virtual preparation tooth reduction region boundary 305, thereby generating one or more virtual reduction coping exposed regions 307. The one or more virtual reduction coping exposed regions 307 correspond to the one or more virtual preparation tooth reduction regions 304. For example, FIG. 10 illustrates virtual reduction coping 302 with virtual reduction coping exposed regions 307. In some embodiments, the computer-implemented method can provide a GUI element such as a check box 306 to display the virtual reduction coping 302.

Figure 11:
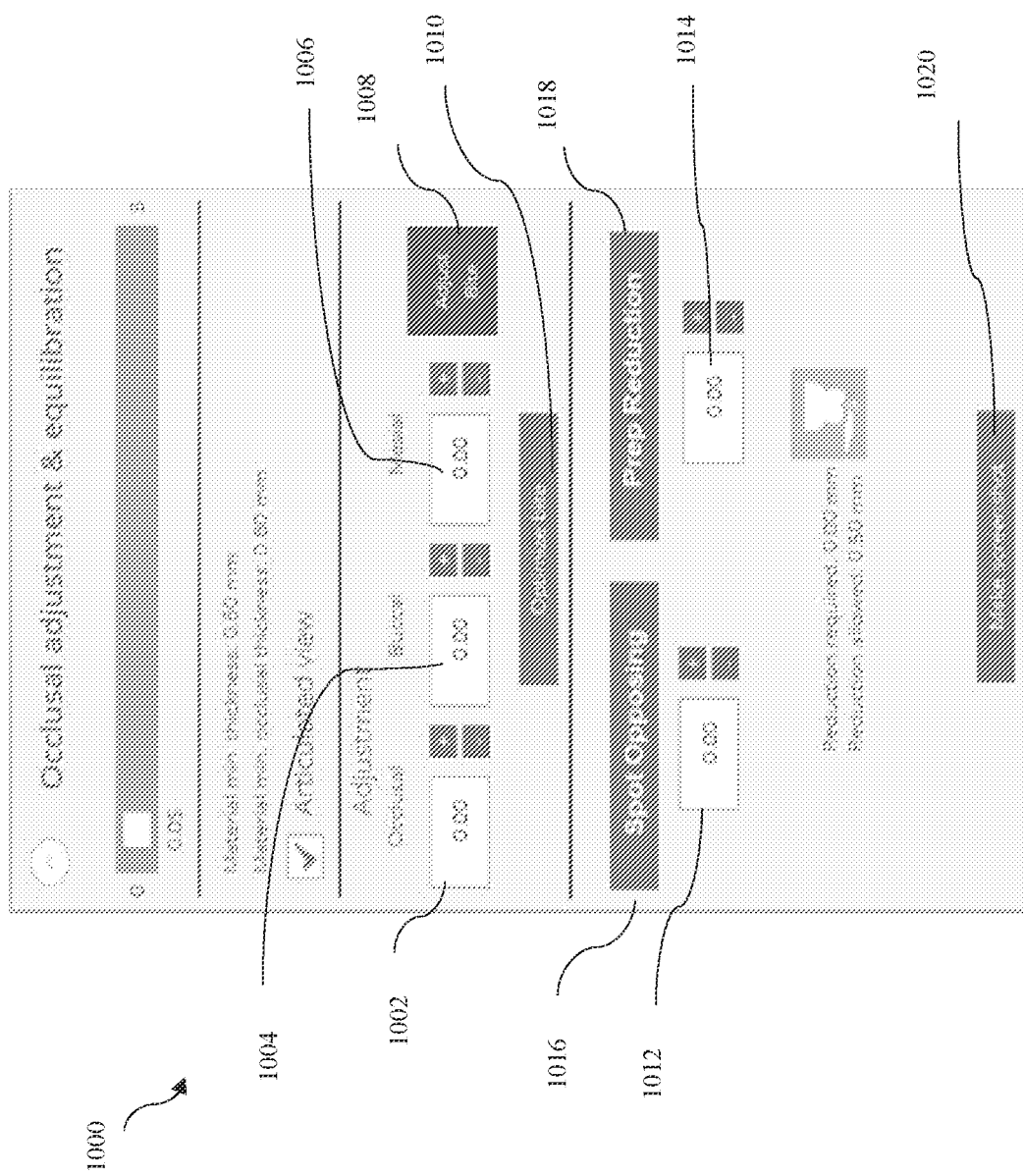
FIG. 11 illustrates a graphic representation of a GUI element provided by a dental design program according to some embodiments.

In another embodiment, FIG. 11 illustrates an example of an interactive GUI 1000 that can be presented on a display. The interactive GUI 1000 can include GUI features such as input fields to adjust the bite and to adjust a reduction amount between a virtual preparation tooth and a virtual opposing tooth in some embodiments, for example. The GUI can include, for example, an occlusal adjustment input field 1002, a buccal adjustment input field 1004, and a mesial adjustment input field 1006. Upon entering adjustment values, a user can trigger a bite adjustment by selecting an adjust bite button 1008, for example, to trigger a bite adjustment in some embodiments. In some embodiments, an optimize bite button 1010 can be selected to automatically adjust the bite, for example. In some embodiments, there may be times when both virtual opposing tooth and virtual preparation tooth reduction is needed, for example. This can happen, in some cases with a severe clearance issue, for example. In some embodiments where too much cannot be reduced from either the virtual opposing tooth or the virtual preparation tooth, a little can be taken from both, for example. In the illustration shown in FIG. 11, for example, the computer-implemented method can in some embodiments display a field to input parameters of how much to reduce from the virtual opposing tooth and the virtual preparation tooth in some embodiments. For example, interactive GUI 1000 can include in some embodiments a spot virtual opposing tooth input field 1012 and a virtual preparation reduction input field 1014. In some embodiments, in everyday use these parameters can default to reduce the entire parameter to either the virtual opposing tooth or the virtual preparation tooth, for example. This can be done in some embodiments, for example, by a tech or user selecting via an input device a spot virtual opposing button 1016 or a virtual preparation tooth reduction button 1018. For example, if case A needs 0.2 mm more clearance, the tech can choose the spot virtual opposing button 1016 and the spot virtual opposing input field 1012 will autofill to 0.2 mm. If case B needs 0.3 mm more clearance, then the tech can choose the virtual preparation tooth reduction button 1018, and the virtual preparation tooth reduction input field 1014 amount will autofill to 0.3 mm. If case C needs 0.9 mm more clearance, then the tech can enter or using arrows increase/decrease the virtual opposing tooth input field 1012 to 0.5 mm, and enter or using arrows increase/decrease the virtual preparation tooth reduction input field 1014 to 0.4 mm. If virtual preparation reduction is selected, the computer-implemented method can in some embodiments automatically generate a simple virtual coping that will fit over the newly prepped die/preparation tooth. In some embodiments, the computer-implemented method can use the same concept as simple virtual coping generation. The computer-implemented method can create a virtual guidance/coping after the virtual preparation tooth has been reduced in some embodiments. The computer-implemented method can create a hole (exposed region) in the virtual reduction coping in some embodiments. In some embodiments, the hole can be the exact area that was reduced for more clearance, for example. In some embodiments, the hole can be used as a visual identifier for a doctor to know where to reduce the physical virtual preparation tooth. In some embodiments, the virtual guidance/reduction coping will not fit until enough virtual preparation tooth has been reduced, for example. In some embodiments, STL can be output in Milling Folder, for example. This can be used to 3D Print to send to the doctor in some embodiments, for example. Screenshots can be made in some embodiments if the user selects a make screenshot button 1020, for example, or can be auto-generated in some embodiments, for example.

Figure 12:
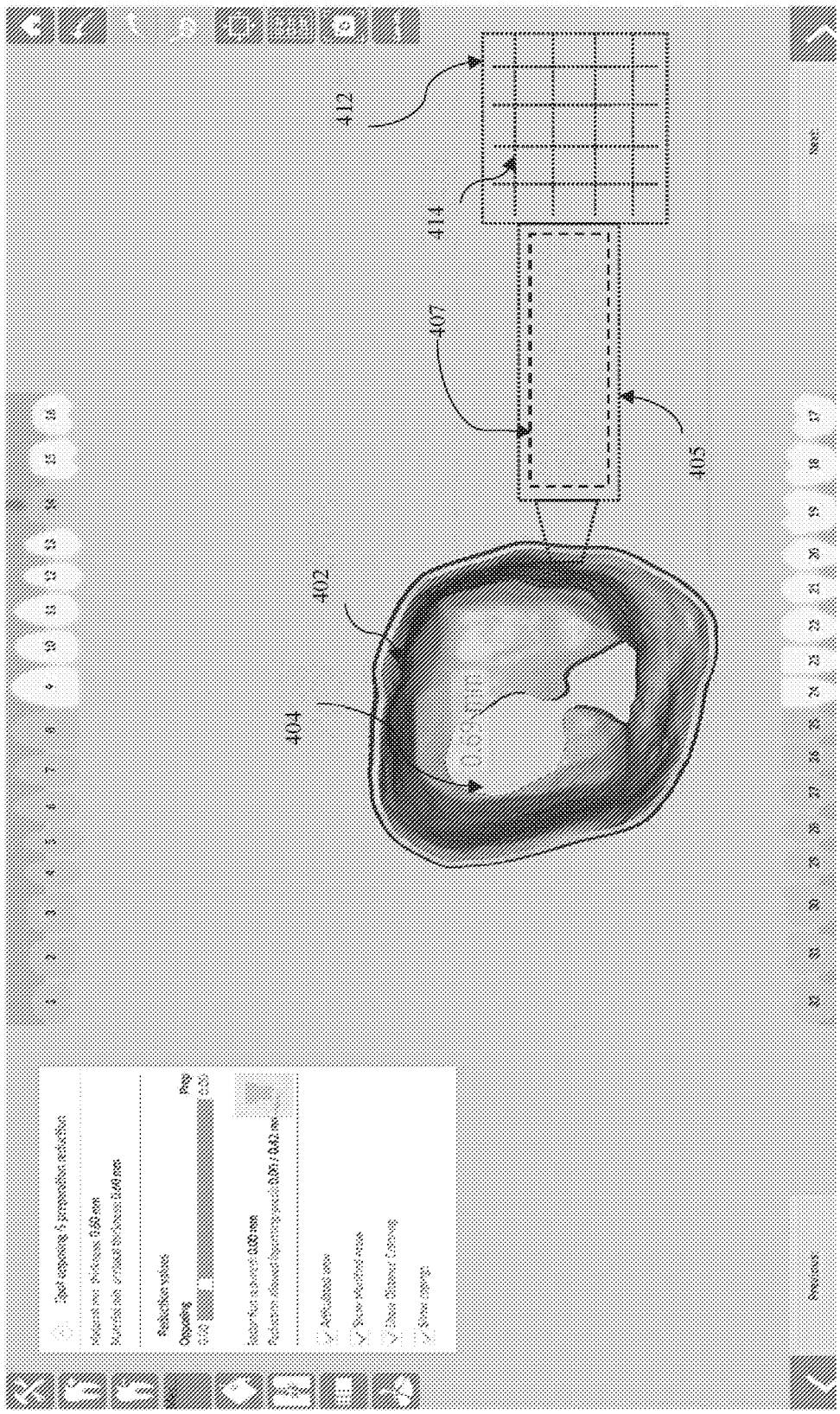
FIG. 12 illustrates a graphic representation of a digital model with a virtual guidance/reduction coping and an illustration of a handle provided by a dental design program according to some embodiments.

FIG. 12 illustrates a generated virtual reduction coping 402 with virtual reduction coping exposed region 404, for example. The virtual coping exposed region 404 can correspond to virtual preparation tooth reduction regions to address virtual occlusal clearance issues and point of insertion issues.

Figure 13:
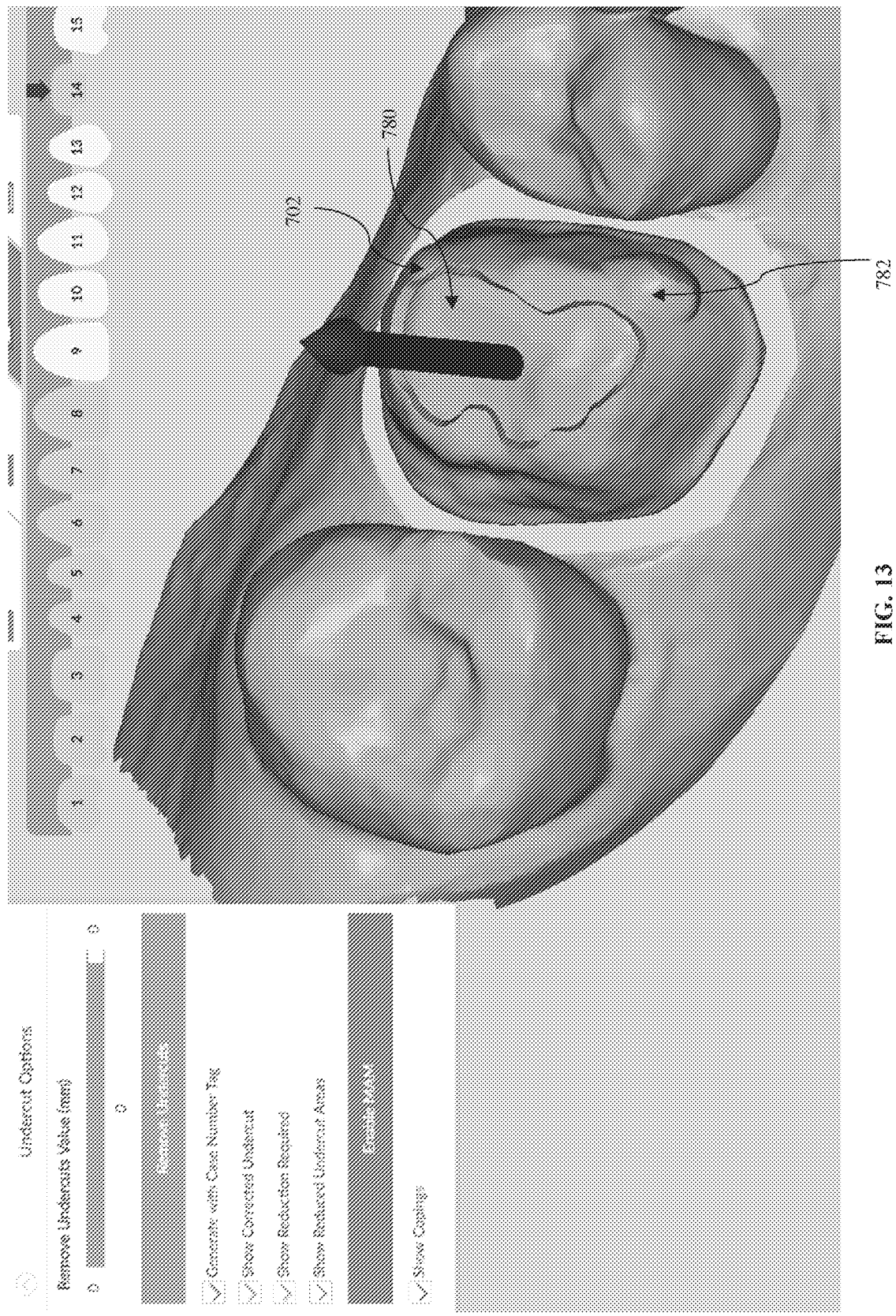
FIG. 13 illustrates a graphic representation of a digital model with a virtual guidance/reduction coping provided by a dental design program according to some embodiments.

For example, as illustrated in FIG. 13, virtual reduction coping 702 includes a first virtual reduction coping exposed region 780 and a second virtual reduction coping exposed region 782. The first virtual reduction coping exposed region 780 can correspond to a virtual preparation tooth reduction region related to an insufficient clearance and the second virtual reduction coping exposed region 782 can correspond to a virtual preparation tooth reduction region related to an insufficient path of insertion. A single virtual reduction coping can thus account for all necessary virtual reduction regions, whether from an insufficient clearance between one or more surfaces of the virtual preparation tooth and one or more opposing dental features, or whether from detecting an insufficient path of insertion. The single virtual reduction coping can thus provide all of the reduction regions necessary in some embodiments for a physical preparation tooth to receive a restoration, for example.

In some embodiments, the computer-implemented method can generate a virtual handle connected with the virtual reduction coping. FIG. 12 illustrates an example of a virtual handle 405 connected to the virtual reduction coping 402 and having one or more virtual identifier regions 407. Also illustrated is an optional virtual barcode region 412 and an optional virtual data matrix 414. FIG. 12 is for illustration purposes only. The virtual handle 405, one or more virtual identifier regions 407, virtual barcode region 412, and virtual data matrix 414 may not be displayed to the user in some embodiments, for example, and can be automatically generated without being displayed. The virtual handle 405 may be automatically generated when a user selects generating the physical reduction coping from the virtual reduction coping 402, for example. In some embodiments, the user selecting 3D printing the virtual reduction coping 402 can trigger the computer-implemented method to automatically generate virtual handle 405. In some embodiments, the virtual handle can optionally include one or more virtual identifier regions 407. In some embodiments, the virtual handle 405 can be integrally connected to the virtual reduction/guidance coping 402. In some embodiments, the computer-implemented method auto generates a case number tag and integrates the case number into the virtual handle 405, for example, in the one or more virtual identifier regions 407. In some embodiments, the computer-implemented method arranges the virtual handle 405 location on the virtual reduction coping by avoiding virtual reduction coping exposed regions. For posterior virtual preparation teeth, the virtual handle 405 can be arranged to be on the lingual side. For anterior virtual preparation teeth, the virtual handle 405 can be arranged on the facial side.

In some embodiments, the computer-implemented method can generate an output file readable by an additive manufacturing process to generate a physical reduction coping with a physical handle from the virtual reduction coping and the virtual handle. The guidance coping can be generated as a water-tight PLY file, which can be 3D printable via a resin or metal based printers. In some embodiments, this can refer to processes by which digital three-dimensional (3D) design data is used to build up a component in layers by depositing material. In some embodiments, several additive manufacturing processes suitable for manufacturing articles can include many polymeric, ceramic, resin, metal, and composite materials, for example. In some embodiments, the material for the reduction coping and optional handle and optional barcode region can be any material suitable for intraoral use, including but not limited to FDA-approved materials for intraoral use.

In some embodiments, additive manufacturing processes can fall into several example categories, including but not limited to vat photopolymerisation, material jetting, binder jetting, material extrusion (e.g., fuse deposition modelling (FDM)), powder bed fusion (e.g., direct metal laser sintering (DMLS), electron beam melting (EBM), selective heat sintering (SHS), selective laser melting (SLM), and selective laser sintering (SLS)), sheet lamination (e.g., ultrasonic additive manufacturing (UAM) and laminated object manufacturing (LOM)), directed energy deposition, and stereolithography, for example. Other additive manufacturing processes are also contemplated.

For example, in some embodiments, the computer-implemented method can generate a STL or PLY file readable by the additive manufacturing process. In some embodiments, an identifier can be integrated with the physical handle made out of the same material as the physical reduction coping and the physical handle. The size of the physical handle can depend on the size of the identifier, in some embodiments. In some embodiments, the virtual reduction coping and virtual handle can be generated into the physical reduction coping and physical handle by the additive manufacturing process together to form a single, integral physical unit. In some embodiments, the additive manufacturing process can utilize metal or resin for the reduction coping/handle. In some embodiments, the material for the physical reduction coping and optional physical handle can be any material suitable for intraoral use, including but not limited to FDA-approved materials for intraoral use. In some embodiments, the computer-implemented method can generate the physical reduction coping and optional handle and optional identifier region(s) using an additive manufacturing process. Any additive manufacturing process can be used.

One example of an additive manufacturing process in some embodiments can include 3D printing. In some embodiments, the computer-implemented method can generate an output file readable by a 3D printer to 3D print the virtual reduction coping and virtual handle and virtual identifier region(s) into the physical reduction coping and connected physical handle, for example. In some embodiments, the 3D printer can utilize metal or resin material for the physical reduction coping, optional physical handle, and optional identifier region(s). Other types of additive processes known in the art can also be used.

In some embodiments, the computer-implemented method can generate an output file readable by a 3D printer to 3D print the virtual reduction coping and virtual handle into the physical reduction coping and connected physical handle.

Figure 14:
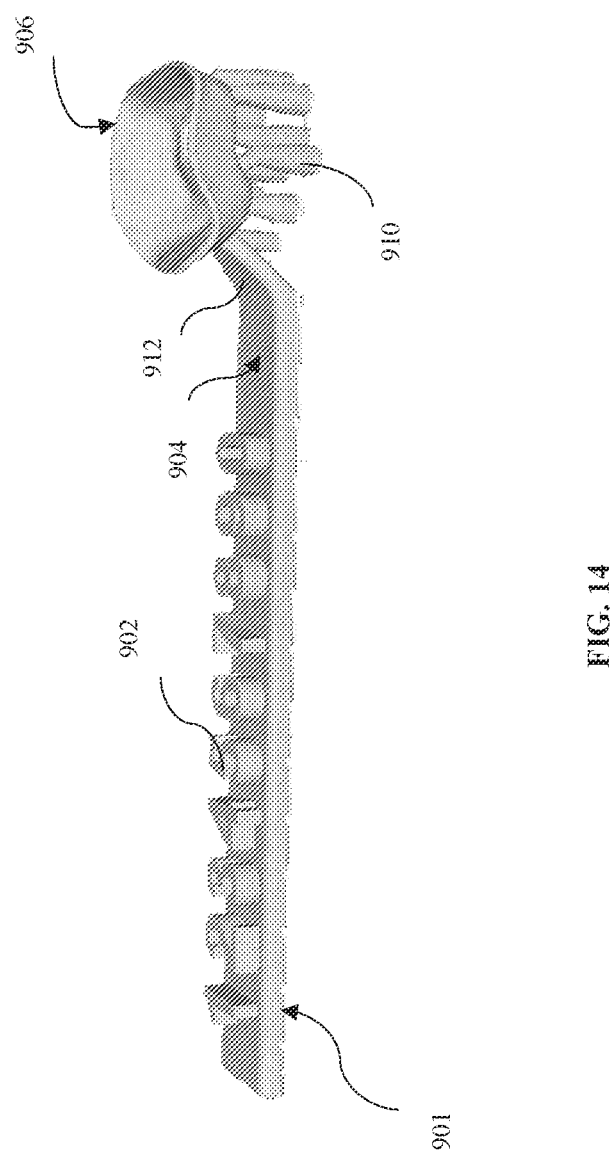
FIG. 14 is an illustration of a physical reduction/guidance coping in with a handle in some embodiments.

In some embodiments, the computer-implemented method can automatically generate a physical handle 901 that is large enough to contain physical identifier 902 to identify the case as illustrated in FIG. 14. An example of a physical coping with a physical handle and physical identifier 902 is illustrated in FIG. 14. The physical identifier 902 can include any alphanumeric and/or symbolic characters and can be in any language.

In some embodiments, the physical handle 901 should point facial or labial in design so it is oriented to point out of the patients mouth when in use so as to accomplish its secondary function, for example. FIG. 14 illustrates the physical handle 901 having the handle base 904 with optional physical identifier region 902. In some embodiments, the base 904 can be angled 912 up to the physical reduction coping 906. This can minimize the number of one or more sprues 910 along the handle base 904, for example. In some embodiments, the handle can also be adjusted to minimize the need for supports. In some embodiments, one or more sprues 910 can be a length that allows the guidance/reduction coping to sit flat on a surface, for example. In some embodiments, the sprues 910 are removable, and can be removed prior to use by a dentist, for example. As seen in FIG. 14, the flat surface of the handle is moved to the minimum point in z to negate the need to support it as it is in direct contact with the base 904, for example. This is a secondary benefit.

Figure 15:
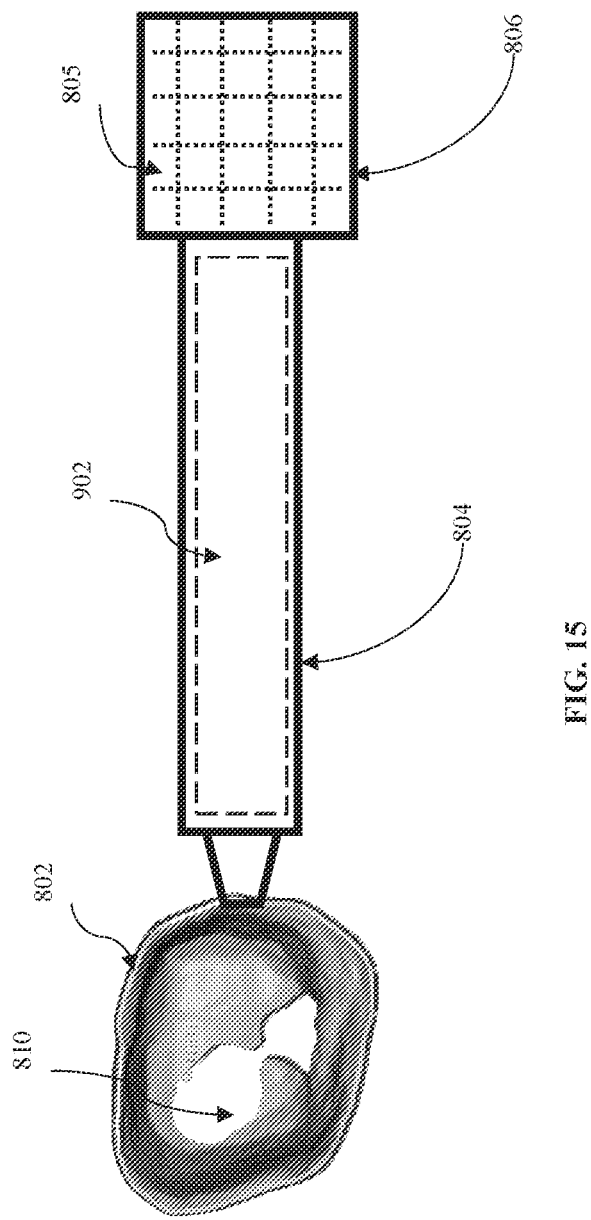
FIG. 15 is an illustration of a physical reduction/guidance coping in with a handle in some embodiments.

FIG. 15 is an illustration of an example of a physical reduction/guidance coping 802 with one or more exposed regions 810 having an optional physical handle 804 with an optional physical identifier 902 and/or an optional physical barcode region 806 with an optional physical data matrix 805. In some embodiments, the physical identifier 902 could also be replaced with a barcode and the optional physical barcode region 806 modified to accommodate the data matrix 805 as seen in FIG. 15, as an example. The data matrix 805 can optionally be computer-readable. The physical barcode region 806 can be of any dimensions. One example in some embodiments the physical barcode region 806 can be dimensioned to accommodate, for example, a 10×10 barcode, for example. The physical data matrix 805 and/or the physical identifier 902 can be based on a case number and/or one or more identifying features that can help track the physical guidance/reduction coping 802 in a production or other environment, for example. FIG. 15 illustrates an example in some embodiments of the optional physical handle 804 attached to the physical reduction coping 802. In some embodiments, the physical reduction/guidance coping 802, optional physical handle 804, optional physical identifier 902, optional physical barcode region 806, and/or optional physical data matrix 805 can be integrally formed and/or connected together and/or made of the same material.

One or more of the features disclosed herein can be combined to form various embodiments. The terms reduction coping and guidance coping can be used interchangeably and can refer to a reduction/guidance coping.

In some embodiments, one or more features herein can virtually reduce the virtual preparation tooth and design a virtual guidance/reduction coping from the virtual model. When printing a physical guidance/reduction coping in a high volume production environment where several different patient copings are produced at once, it can be challenging and error prone to identify each one. In some embodiments, one or more features disclosed herein can integrate an identifier where a code corresponding to the case can be added which may be human readable or a bar/QR code or something similar. Another problem with reduction copings is that they are very small and difficult to handle and often need to be taken in and out of the patients mouth many times during the reduction process. In some embodiments, the space to add an identifier also forms/serves as a handle for the doctor or others to use, for example.

Figure 16:
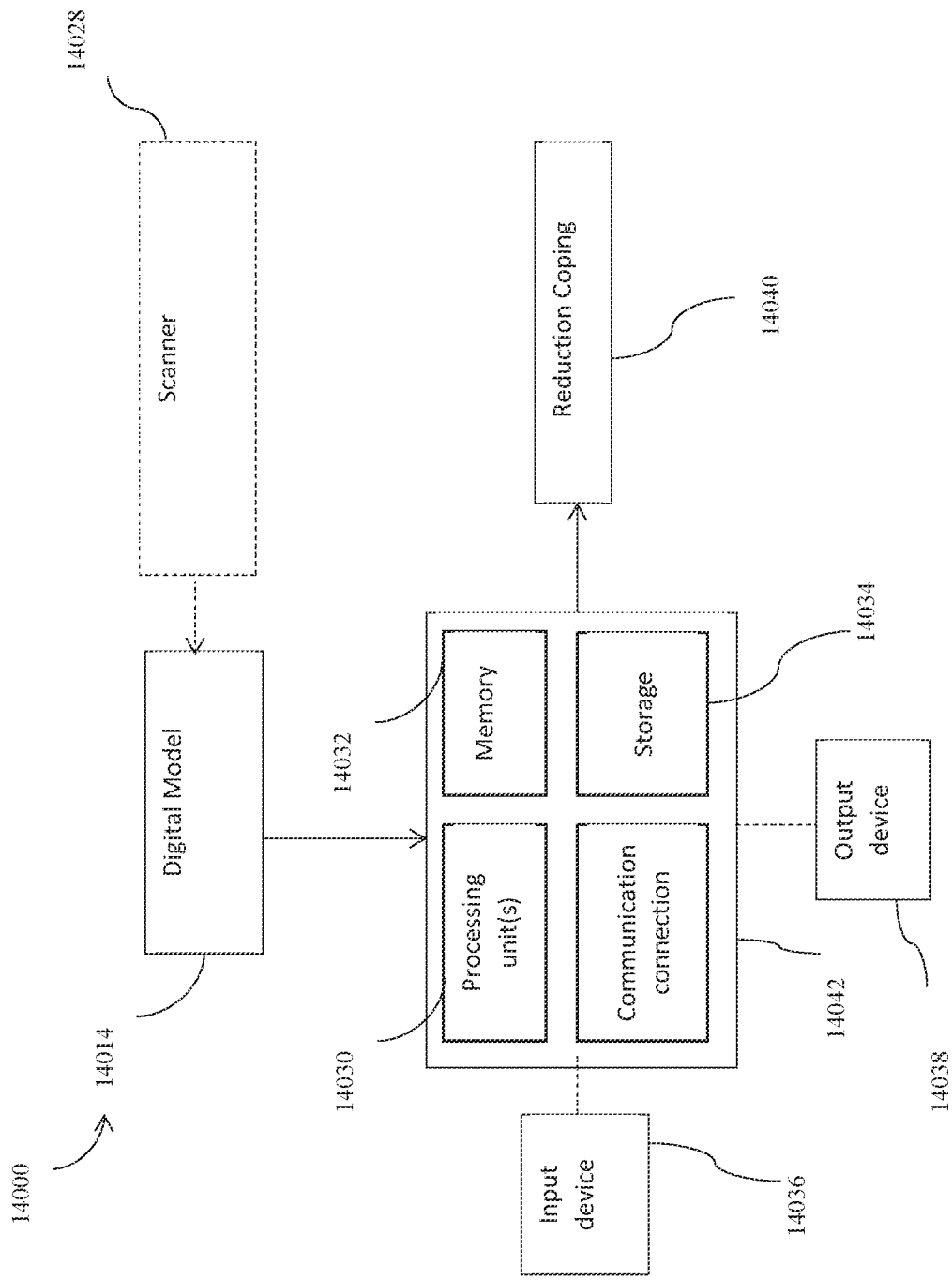
FIG. 16 is a diagram of a system in some embodiments.

FIG. 16 illustrates a digital impression processing system 14000 in some embodiments. The system 14000 can include a processor 14030, computer-readable storage medium 14034 having instructions executable by the processor to perform steps including one or more features described in the present disclosure. In some embodiments, the system 14000 can provide at 14040 a reduction coping that can be virtual and/or physical, that can be with or without a handle (with or without one or more identifiers), and/or an output file for an additive manufacturing process to generate a physical reduction coping with or without a physical handle (with or without one or more identifiers), for example. In some embodiments, the additive manufacturing process can include 3D printing. In some embodiments, an optional 3D printer can also be used. Other outputs are possible, and these are only provided as examples. Scanner 14028 is optional and shown only for illustration purposes as an example. The scanner 14028 can be an optical and/or x-ray based CT scanning system, for example, and can generate the digital model 14014.

Some embodiments include a processing system for generating a reduction coping. The system can include, for example, a processor, a computer-readable storage medium including instructions executable by the processor to perform steps including: receiving a digital model comprising a virtual preparation tooth, determining one or more virtual reduction regions on the virtual preparation tooth; and generating a virtual reduction coping comprising one or more exposed regions corresponding to the one or more virtual reduction regions.

FIG. 16 illustrates a processing system 14000 in some embodiments. The system 14000 can include a processor 14030, computer-readable storage medium 14034 having instructions executable by the processor to perform one or more steps described in the present disclosure. The digital model can optionally be provided by an optional scanner 14028, for example. The system 14000 can provide a guidance/reduction coping 14040. In some embodiments, the guidance/reduction coping 14040 can be a digital model of the guidance/coping. In some embodiments, the guidance/reduction coping 14040 can be suitable for use with an additive manufacturing process such as 3D printing to generate a physical guidance/reduction coping.

Figure 17A:
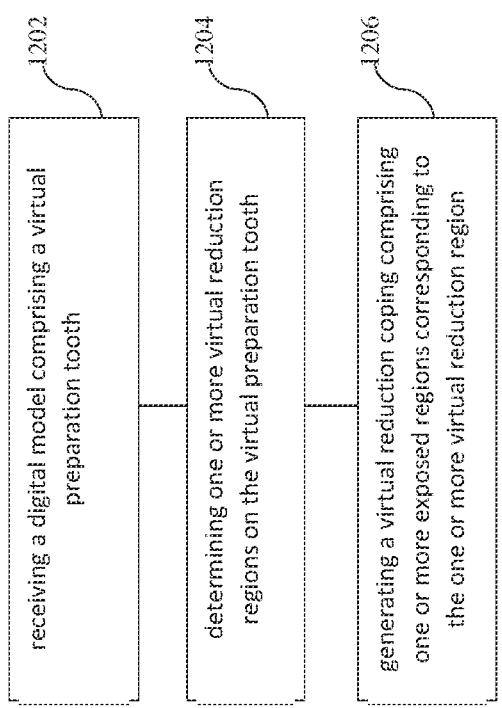
FIGS. 17(a) and 17(b) are flow charts illustrating examples of methods in some embodiments.

FIG. 17(a) illustrates an example of a computer-implemented method of generating a reduction coping. The computer-implemented method can include, for example, receiving a digital model comprising a virtual preparation tooth at 1202, determining one or virtual reduction regions on the virtual preparation tooth at 1204, and generating a virtual reduction coping comprising one or more exposed regions corresponding to the one or more virtual reduction regions at 1206.

The method can include one or more of the following optional features in some embodiments, for example. For example, the method can further include generating a virtual handle affixed to the virtual reduction coping. The method can further include generating a physical reduction coping and physical handle from the virtual reduction coping and the virtual handle. The virtual handle can include at least one identifier region. Determining one or more necessary virtual reduction regions can include detecting an insufficient clearance between one or more surfaces of the virtual preparation tooth and one or more other dental features. The method can further include detecting an insufficient virtual occlusal clearance. Detecting an insufficient virtual occlusal clearance can include determining that a virtual occlusal clearance between one or more virtual preparation tooth occlusal surfaces and one or more virtual opposing tooth occlusal surfaces is less than a minimum required occlusal clearance. The minimum required occlusal clearance can include a minimum restoration thickness. The computer-implemented method can determine the minimum restoration thickness automatically based on the restoration type selected. The minimum required occlusal clearance can further include an adhesive thickness. The method can further include determining a total virtual reduction amount necessary to satisfy the minimum required occlusal clearance. The total virtual reduction amount can be a difference between the virtual occlusal clearance and the minimum required occlusal clearance. The method can further include displaying a GUI element to the user to allow adjusting a distribution of the total virtual reduction amount between a virtual preparation tooth reduction amount and a virtual opposing tooth reduction amount. The method can further include determining a virtual margin around the virtual preparation tooth. Determining one or more necessary virtual reduction regions can include detecting an insufficient path of insertion between one or more side surface regions of the virtual preparation tooth and the virtual margin boundary. The virtual preparation tooth side surface regions to reduce can be part of the virtual preparation tooth reduction regions. The method can further include virtually reducing the virtual preparation tooth reduction regions by the virtual preparation tooth reduction amount and virtually reducing the virtual preparation tooth side surface regions by the virtual preparation tooth side surface reduction amount.

Figure 17B:
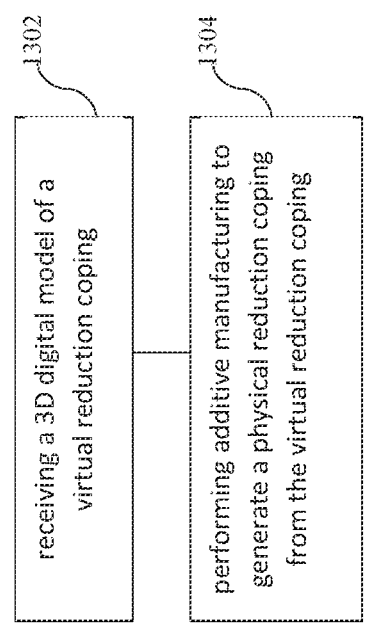

FIG. 17(b) illustrates a method of generating a physical reduction coping. The method can include, for example, receiving a 3D digital model of a virtual reduction coping at 1302 and performing additive manufacturing to generate a physical reduction coping from the virtual reduction coping at 1304.

The method can include one or more features as disclosed herein, including but not limited to the following features in some embodiments. For example, performing additive manufacturing can include 3D printing the physical reduction coping. The physical reduction coping can include an integrated physical handle. The integrated physical handle can include an identifier. The physical reduction coping can include one or more exposed regions corresponding to one or more virtual preparation tooth reduction regions.

In some embodiments, generating a guidance/reduction coping can be initiated by a user using one or more features disclosed herein, for example. In some embodiments, generating a guidance/reduction can include one or more of the features described in the present disclosure. In some embodiments, generating a guidance/reduction coping can be performed by a user using an input device while viewing the digital model on a display, for example. In some embodiments, the computer-implemented method can allow the input device to manipulate the digital model displayed on the display. For example, in some embodiments, the computer-implemented method can rotate, zoom, move, and/or otherwise manipulate the digital model in any way as is known in the art. In some embodiments, generating a guidance/reduction can be performed by a user using the input device. In some embodiments, generating a guidance/reduction can be initiated, for example, using techniques known in the art, such as a user selecting a button.

One or more features shown on a GUI can be selected using an input device whose pointer is shown on a display for example. The pointer can be used to select a region of one point by clicking on an input device such as a mouse or tapping on a touch screen for example. A digital surface of multiple points can be selected by dragging the pointer across a digital surface, in some embodiments, for example. Other techniques known in the art can be used to select a point or digital surface. In some embodiments, can be performed by a user using an input device and viewing the digital model a display, for example.

In some embodiments the computer-implemented method can display a digital model on a display and receive input from an input device such as a mouse or touch screen on the display for example. The computer-implemented method can, upon receiving an initiation command, generate a virtual and/or physical guidance/reduction coping with an optional handle and an optional identifier using one or more features described in the present disclosure. The computer-implemented method can, upon receiving manipulation commands, rotate, zoom, move, and/or otherwise manipulate the digital model in any way as is known in the art.

One advantage of one or more features of the present disclosure can include automatic generation of a 3D printable virtual reduction coping with a handle having an optional identifier, for example. This can, for example, provide a way to automate production of physical reduction/guidance copings from digital dental impressions/models, for example. Another advantage of one or more features as disclosed can include the ability to identify and track guidance/reduction copings which can help in high production environments, for example. Another advantage of one or more features can include making the reduction coping easier to handle, for example. Another advantage of one or more features of the present disclosure can include, for example, a more accurate reduction coping that evaluates and accounts for reduction areas due to insufficient occlusal clearance and path of insertion clearance. Another advantage of one or more features of the present disclosure can include, for example, generating a virtual guidance/reduction coping directly from digital models produced by intraoral scans and/or scans of physical impressions. This can, for example, advantageously allow generating a virtual guidance/reduction coping without a stone model. This can also, for example, advantageously eliminate the step of having to physically print the model or requiring a stone model to thermoform or wax the coping. Another advantage can include, for example, allowing a technician to adjust a distribution of the reduction amount between the virtual opposing tooth and a virtual preparation tooth. Another advantage of one or more features of the present disclosure can include, for example, providing a 3D printable virtual reduction coping and optional handle and optional identifier that can be integrally connected using the same material.

One or more of the features disclosed herein can be performed and/or attained automatically, without manual or user intervention. One or more of the features disclosed herein can be performed by a computer-implemented method. The features—including but not limited to any methods and systems—disclosed may be implemented in computing systems. For example, as illustrated in FIG. 16, the computing environment 14042 used to perform these functions can be any of a variety of computing devices (e.g., desktop computer, laptop computer, server computer, tablet computer, gaming system, mobile device, programmable automation controller, video card, etc.) that can be incorporated into a computing system comprising one or more computing devices. In some embodiments, the computing system may be a cloud-based computing system.

For example, a computing environment 14042 may include one or more processing units 14030 and memory 14032. The processing units execute computer-executable instructions. A processing unit 14030 can be a central processing unit (CPU), a processor in an application-specific integrated circuit (ASIC), or any other type of processor. In some embodiments, the one or more processing units 14030 can execute multiple computer-executable instructions in parallel, for example. In a multi-processing system, multiple processing units execute computer-executable instructions to increase processing power. For example, a representative computing environment may include a central processing unit as well as a graphics processing unit or co-processing unit. The tangible memory 14032 may be volatile memory (e.g., registers, cache, RAM), non-volatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage 14034, one or more input devices 14036, one or more output devices 14038, and one or more communication connections 14037. An interconnection mechanism such as a bus, controller, or network, interconnects the components of the computing environment. Typically, operating system software provides an operating environment for other software executing in the computing environment, and coordinates activities of the components of the computing environment.

The tangible storage 14034 may be removable or non-removable and includes magnetic or optical media such as magnetic disks, magnetic tapes or cassettes, CD-ROMs, DVDs, or any other medium that can be used to store information in a non-transitory way and can be accessed within the computing environment. The storage 14034 stores instructions for the software implementing one or more innovations described herein.

The input device(s) may be, for example: a touch input device, such as a keyboard, mouse, pen, or trackball; a voice input device; a scanning device; any of various sensors; another device that provides input to the computing environment; or combinations thereof. For video encoding, the input device(s) may be a camera, video card, TV tuner card, or similar device that accepts video input in analog or digital form, or a CD-ROM or CD-RW that reads video samples into the computing environment. The output device(s) may be a display, printer, speaker, CD-writer, or another device that provides output from the computing environment.

The communication connection(s) enable communication over a communication medium to another computing entity.

The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media 14034 (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media 14034. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, Python, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

In view of the many possible embodiments to which the principles of the disclosure may be applied, it should be recognized that the illustrated embodiments are only examples and should not be taken as limiting the scope of the disclosure.

What is claimed is:

1. A computer-implemented method of generating a reduction coping, comprising:
   receiving a digital model generated from an intraoral scan of a patient's dentition, the digital model comprising a virtual preparation tooth;
   determining one or more virtual reduction regions on the virtual preparation tooth; and
   generating a virtual reduction coping comprising one or more exposed regions corresponding to the one or more virtual reduction regions,
   wherein determining one or more necessary virtual reduction regions comprises:
      detecting an insufficient clearance between one or more surfaces of the virtual preparation tooth and one or more other dental features; and
      detecting an insufficient virtual occlusal clearance,
   wherein detecting an insufficient virtual occlusal clearance comprises determining that a virtual occlusal clearance between one or more virtual preparation tooth occlusal surfaces and one or more virtual opposing tooth occlusal surfaces is less than a minimum required occlusal clearance;
   wherein the minimum required occlusal clearance comprises a minimum restoration thickness,
   wherein the minimum restoration thickness is determined automatically based on a restoration type selected.

2. The method of claim 1, further comprising generating a virtual handle affixed to the virtual reduction coping.

3. The method of claim 2, further comprising generating a physical reduction coping and physical handle from the virtual reduction coping and the virtual handle.

4. The method of claim 2, wherein the virtual handle comprises at least one identifier region.

5. The method of claim 1, wherein the minimum required occlusal clearance further comprises an adhesive thickness.

6. The method of claim 1, further comprising determining a total virtual reduction amount necessary to satisfy the minimum required occlusal clearance.

7. The method of claim 6, wherein the total virtual reduction amount is a difference between the virtual occlusal clearance and the minimum required occlusal clearance.

8. The method of claim 7, further comprising displaying a GUI element to the user to allow adjusting a distribution of the total virtual reduction amount between a virtual preparation tooth reduction amount and a virtual opposing tooth reduction amount.

9. The method of claim 1, further comprising determining a virtual margin around the virtual preparation tooth.

10. The method of claim 9, wherein determining one or more necessary virtual reduction regions comprises detecting an insufficient path of insertion between one or more side surface regions of the virtual preparation tooth and the virtual margin boundary.

11. The method of claim 10, wherein the virtual preparation tooth side surface regions to reduce are part of the virtual preparation tooth reduction regions.

12. The method of claim 11, further comprising virtually reducing the virtual preparation tooth reduction regions by a virtual preparation tooth reduction amount and virtually reducing the virtual preparation tooth side surface regions by a virtual preparation tooth side surface reduction amount.

13. A method of generating a physical reduction coping, comprising:
    receiving a 3D digital model, of a virtual reduction coping; and
    performing additive manufacturing to generate a physical reduction coping from the virtual reduction coping,
    wherein the physical reduction coping comprises one or more exposed regions corresponding to one or more virtual preparation tooth reduction regions,
    wherein the one or more exposed regions correspond to an insufficient occlusal clearance,
    wherein the insufficient virtual occlusal clearance comprises an occlusal clearance between one or more preparation tooth occlusal surfaces and one or more opposing tooth occlusal surfaces being less than a minimum required occlusal clearance,
    wherein the insufficient occlusal clearance comprises a minimum restoration thickness,
    wherein the minimum restoration thickness is determined automatically based on a restoration type selected.

14. The method of claim 13, wherein performing additive manufacturing comprises 3D printing the physical reduction coping.

15. The method of claim 13, wherein the physical reduction coping comprises an integrated physical handle.

16. The method of claim 15, wherein the integrated physical handle comprises an identifier.

\* \* \* \* \*